United States Patent [19]

Torrence et al.

[11] Patent Number: 4,994,608

[45] Date of Patent: Feb. 19, 1991

[54] ADDITION OF HYDROGEN TO CARBON MONOXIDE FEED GAS IN PRODUCING ACETIC ACID BY CARBONYLATION OF METHANOL

[75] Inventors: G. Paull Torrence, Corpus Christi, Tex.; Joel D. Hendricks, Pineville, N.C.; Dennis D. Dickinson; Adolfo Aguilo, all of Corpus Christi, Tex.

[73] Assignee: Hoechst Celanese Corporation, North Somerville, N.J.

[21] Appl. No.: 82,945

[22] Filed: Aug. 5, 1987

Related U.S. Application Data

[63] Continuation of Ser. No. 874,734, Jun. 16, 1986, abandoned.

[51] Int. Cl.$^5$ .................. C07C 51/12; C07C 53/08
[52] U.S. Cl. ...................... 562/519; 203/71; 203/77; 203/88; 260/413; 562/517
[58] Field of Search ............... 562/519, 497, 406, 577

[56] References Cited

U.S. PATENT DOCUMENTS 3,769,329 10/1973 Paulik et al. .................. 562/517
4,374,070 2/1983 Larkins et al. ................. 560/232

FOREIGN PATENT DOCUMENTS 144935 6/1985 European Pat. Off. .
144936 6/1985 European Pat. Off. .
170965 2/1986 European Pat. Off. .
59-53440 3/1984 Japan .
2146637 4/1985 United Kingdom .
2155929 10/1985 United Kingdom .

OTHER PUBLICATIONS

Roth et al., Chem. Tech., vol. 1, Oct. 1971, pp. 600-605.

Primary Examiner—Vivian Garner
Attorney, Agent, or Firm—Depaoli & O'Brien; Donald R. Cassady

[57] ABSTRACT

The carbonylation of an alcohol to produce a carboxylic acid, especially methanol to produce acetic acid, in a low water reaction medium containing a rhodium catalyst stabilized with an iodide salt, especially lithium iodide, along with alkyl iodide such as methyl iodide and alkyl acetate such as methyl acetate in specified proportions is improved by the addition of hydrogen in the feed gas to the low water reaction medium to obtain a reactor hydrogen partial pressure of at least about 4 psi. The presence of hydrogen in the reaction medium increases significantly the carbonylation reaction rate and reduces formation of byproduct carbon dioxide. The present reaction system not only provides an acid product of unusually low water content at unexpectedly favorable reaction rates but also, whether the water content is low or, as in the case of prior-art acetic acid technology, relatively high, is characterized by unexpectedly high catalyst stability; i.e., it is resistant to catalyst precipitation out of the reaction medium.

17 Claims, 26 Drawing Sheets

Rate of Rh Precipitation in the Absence of LiI – Batch Glass Vessel

Rate of Rh Precipitation in the Presence of I⁻ Additives – Batch Autoclave

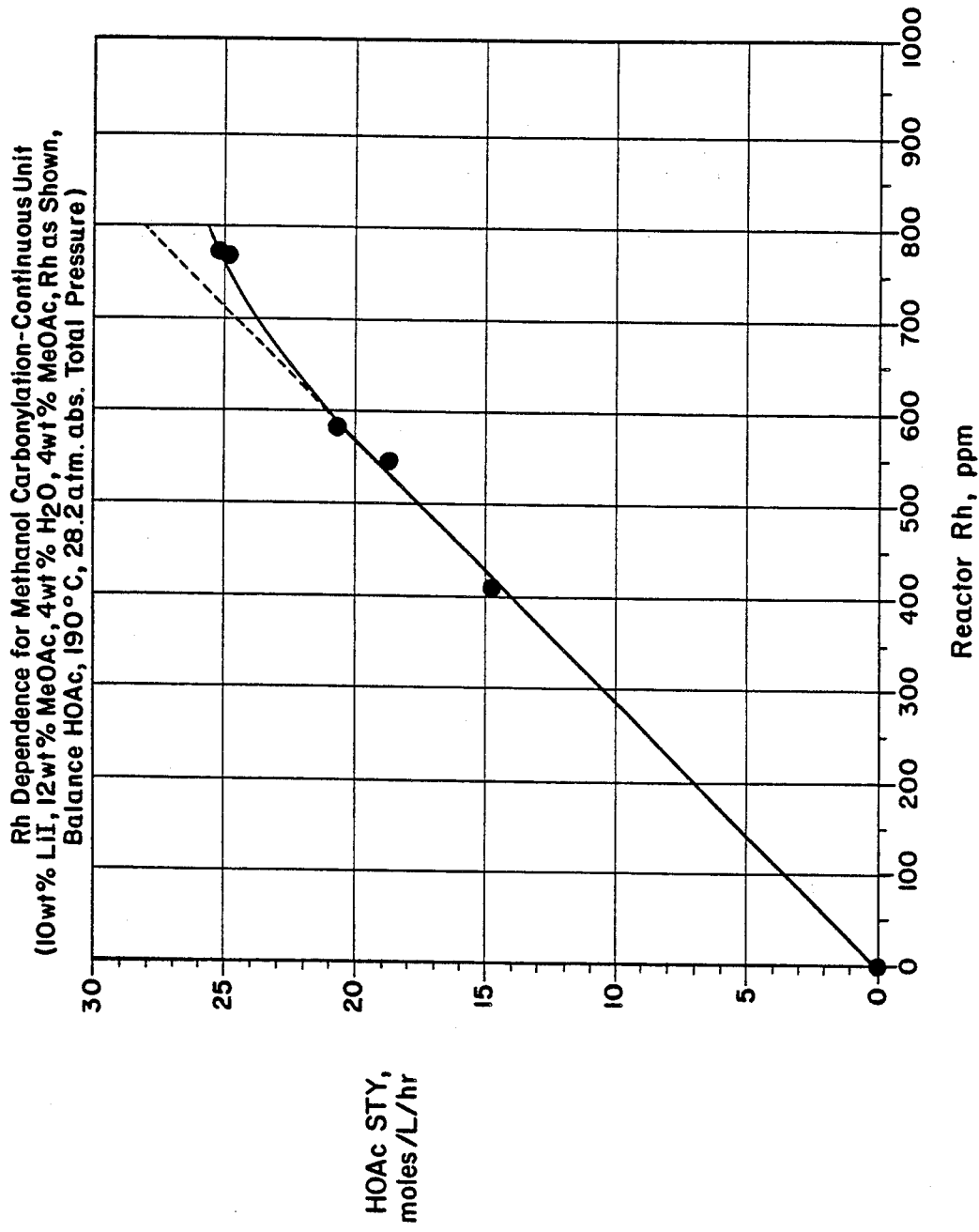

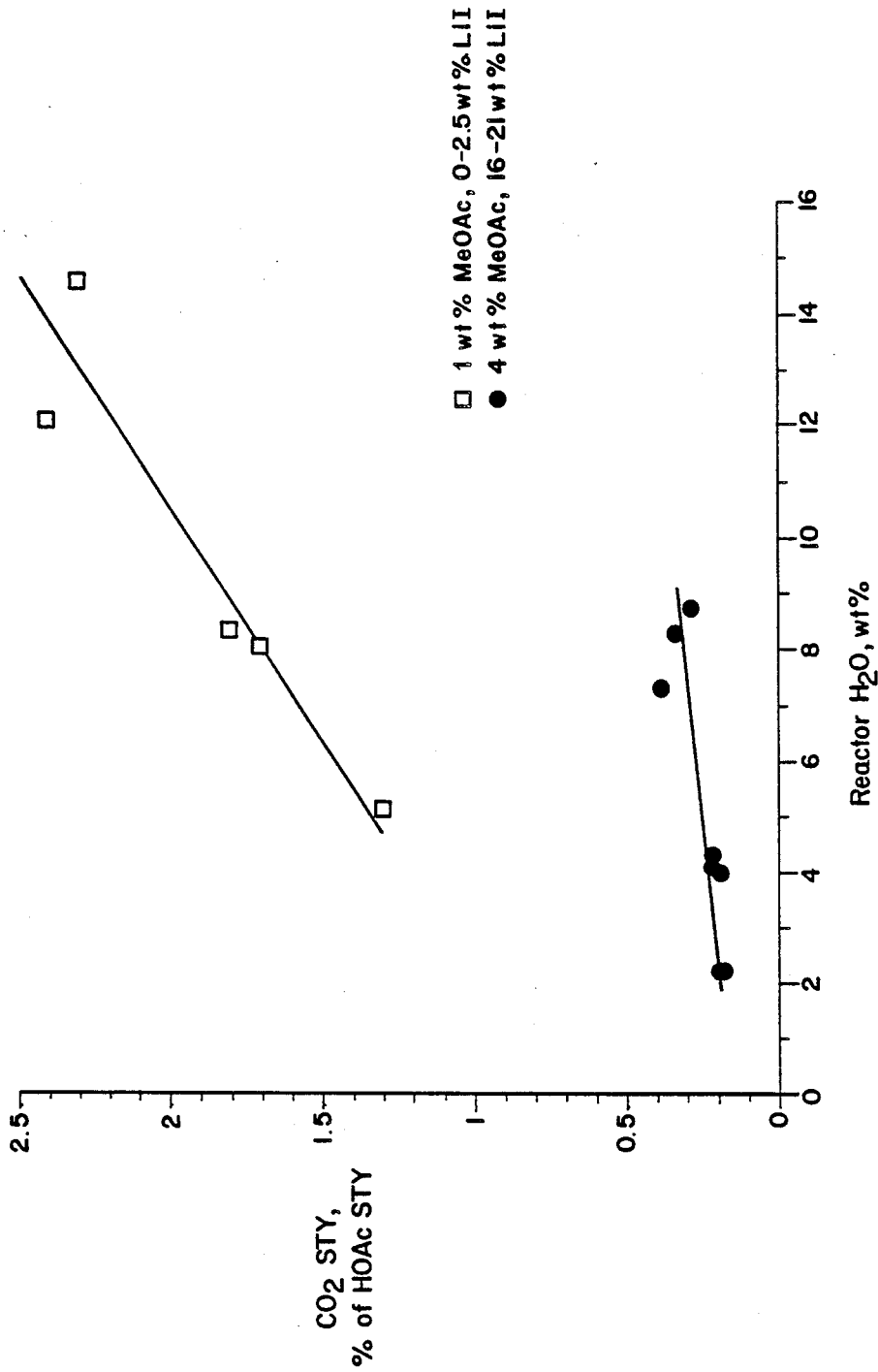

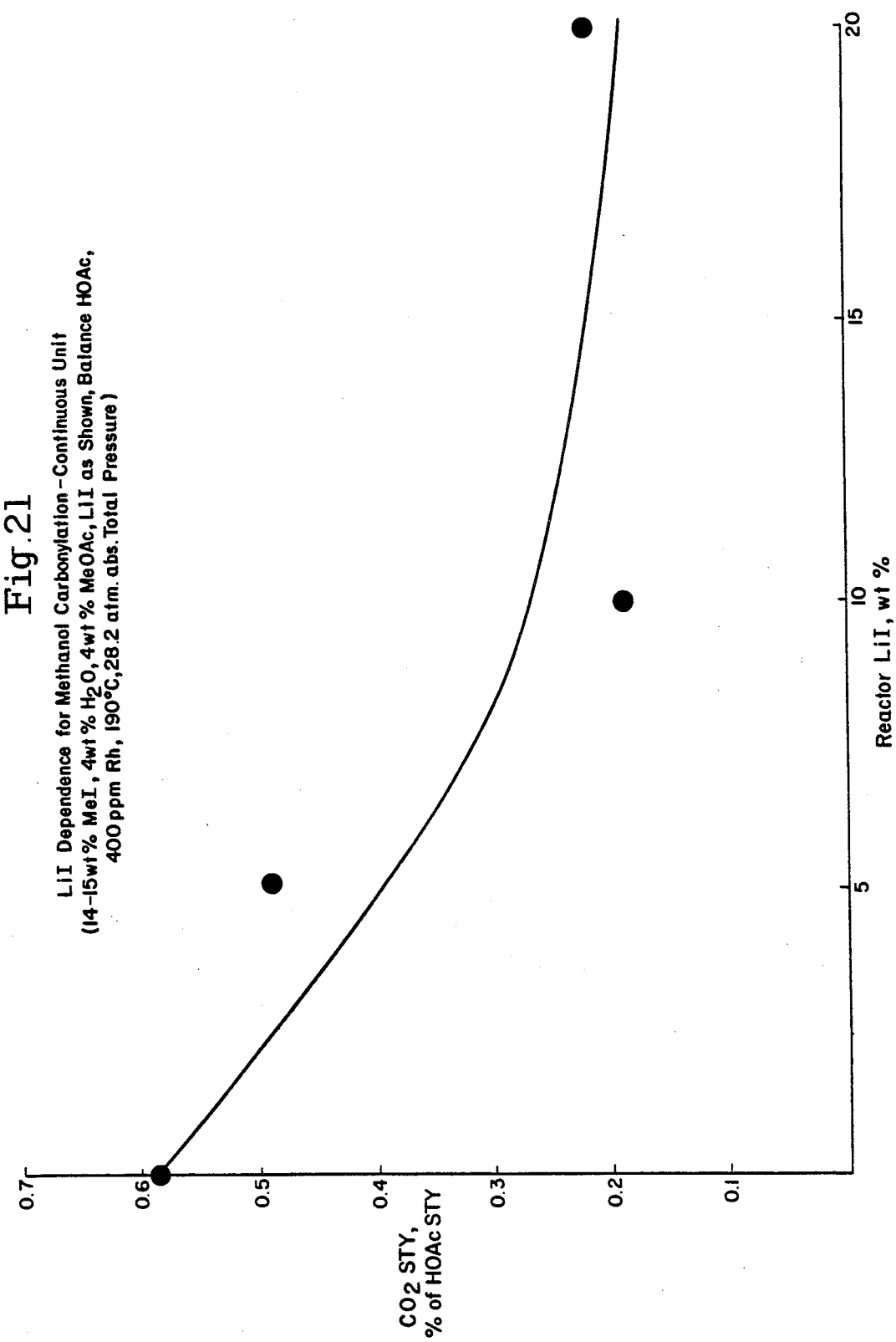

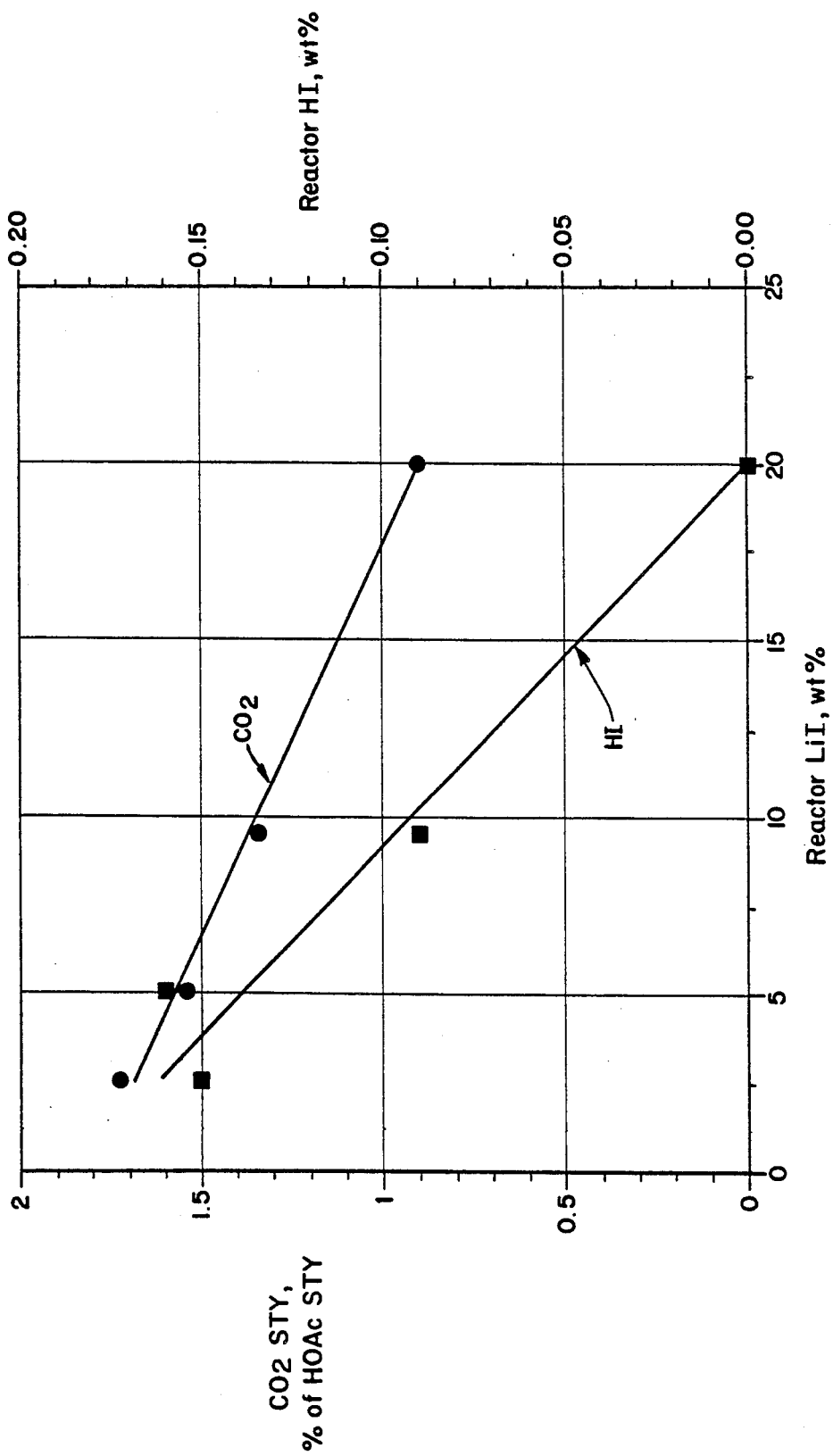

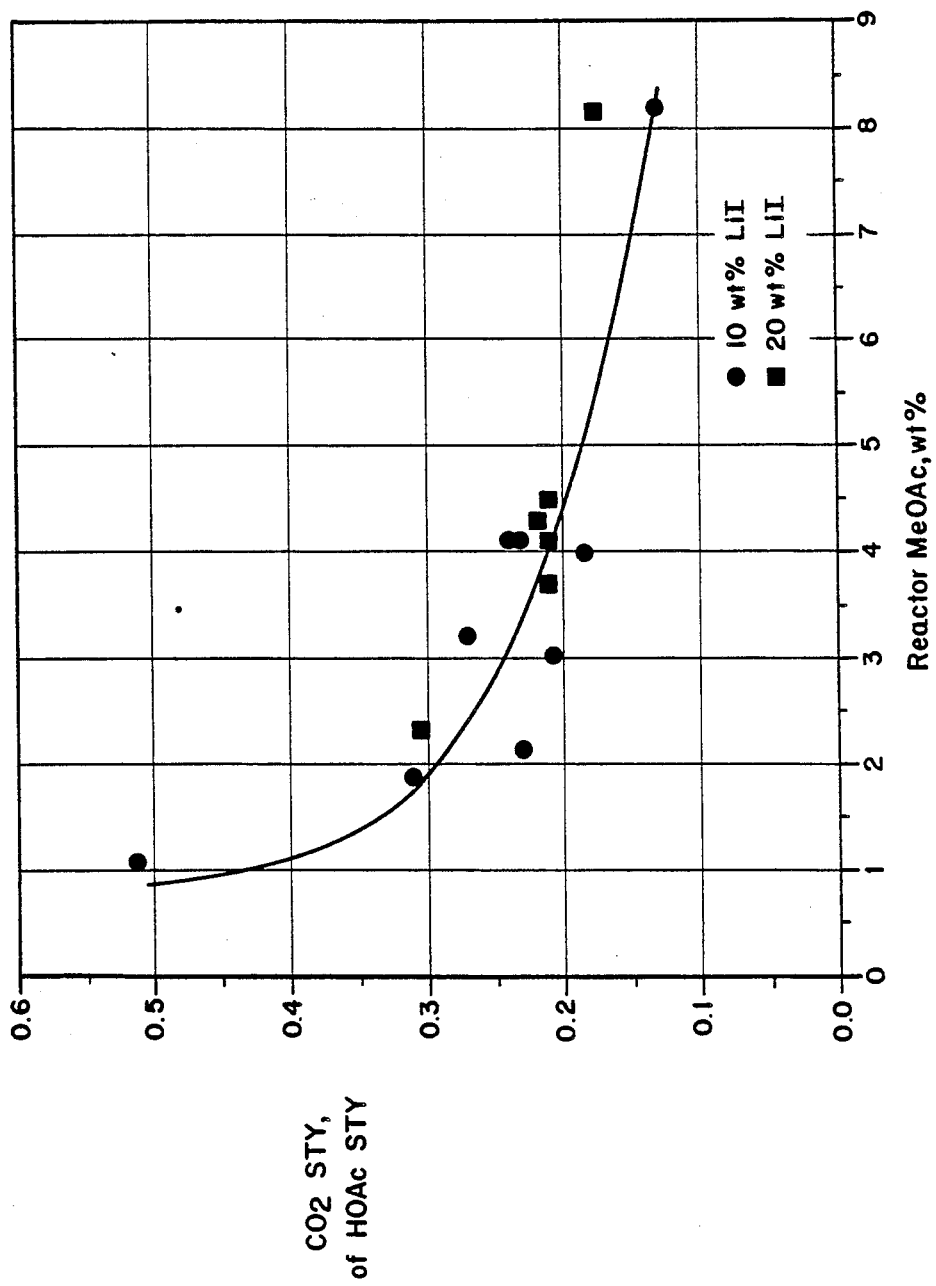

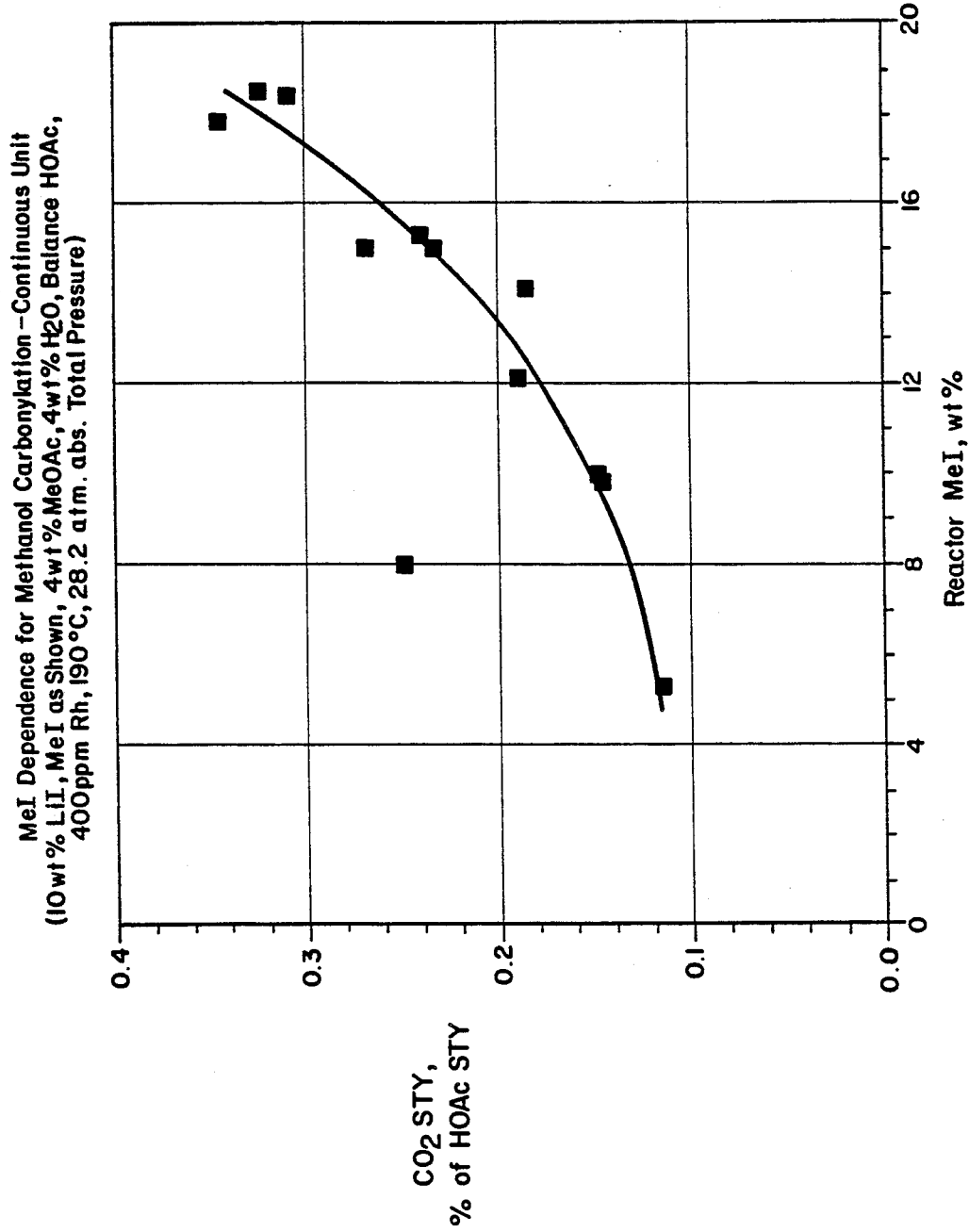

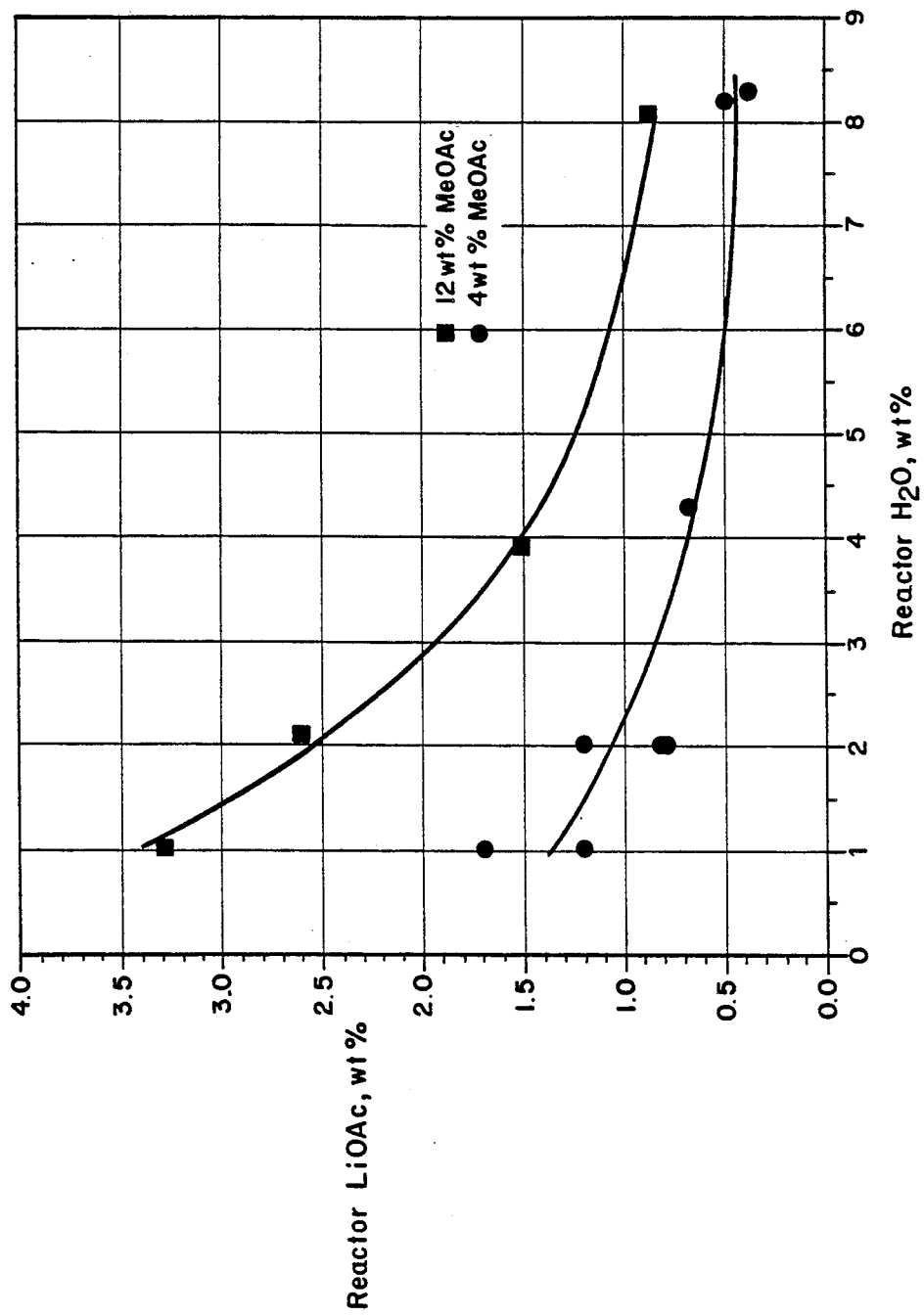

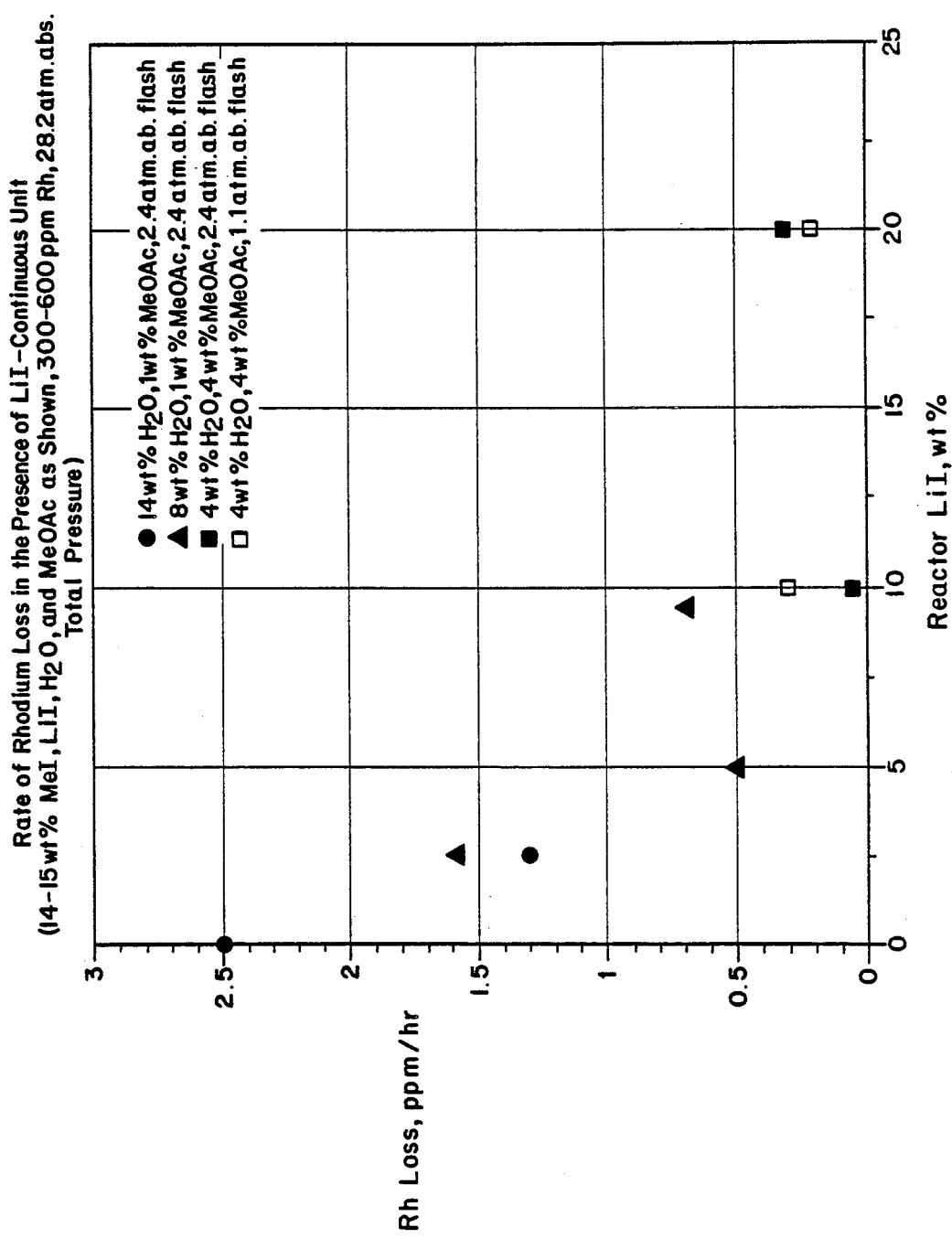

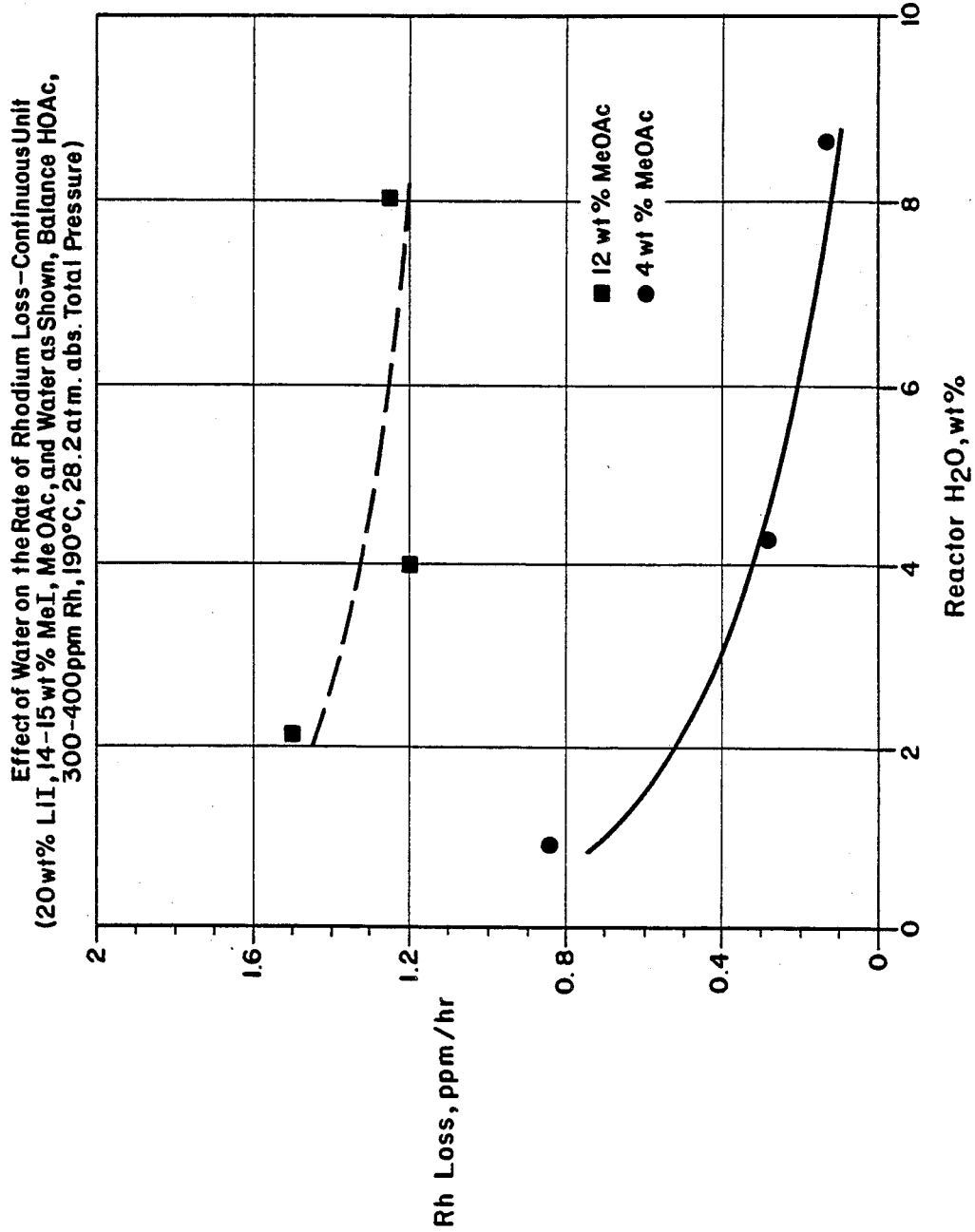

ADDITION OF HYDROGEN TO CARBON MONOXIDE FEED GAS IN PRODUCING ACETIC ACID BY CARBONYLATION OF METHANOL

This application is a continuation of application Ser. No. 874,734, filed June 16, 1986, now abandoned.

BACKGROUND OF THE INVENTION

1. Field of the Invention

This invention concerns an improved process for carbonylating methanol to acetic acid.

2. Description of the Prior Art

Among currently-employed processes for synthesizing acetic acid one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or else supported on an inert solid, along with a halogen-containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. These compounds are employed as promoters, not stabilizers. Most typically and usefully, the reaction is conducted with the catalyst being dissolved in a liquid reaction medium through which carbon monoxide gas is continuously bubbled.

Paulik et al teach that the liquid reaction medium can be any solvent compatible with the catalyst system and that it may comprise, for example, the pure alcohol which is being reacted, or mixtures thereof with the desired carboxylic acid end product and/or esters of these two compounds. However, the patentees teach further that the preferred solvent and liquid reaction medium for the process is the desired carboxylic acid itself, i.e., acetic acid when methanol is being carbonylated to produce acetic acid. Paulik et al also disclose that water may be added to the reaction mixture to exert a beneficial effect upon the reaction rate.

Considering specifically the carbonylation of methanol to acetic acid in a solvent comprising predominantly acetic acid and using the promoted catalyst taught by Paulik et al, it is taught in European patent application 0,055,618 that about 14–15 wt. % water is present in the reaction medium of a typical acetic acid plant using this technology. Recovering acetic acid in anhydrous or nearly anhydrous form from such a reaction solvent and separating the acetic acid from this appreciable quantity of water, involves substantial expenditure of energy in distillation and/or additional processing steps such as solvent extraction, as well as enlarging some of the process equipment as compared with that used in handling drier materials. Also Hjortkjaer and Jensen [*Ind. Eng. Chem., Prod. Res. Dev.* 16, 281–285 (1977)] have shown that increasing the water from 0 to 14 wt. % water increases the reaction rate of methanol carbonylation. Above about 14 wt. % water the reaction rate is unchanged.

Another disadvantage of the carbonylation process as just previously described is that the rhodium catalyst tends to precipitate out of the reaction medium, especially during the course of distillation operations to separate the product from the catalyst solution when the carbon monoxide content of the catalyst system is reduced (EP0,055,618). It has now been found that this tendency increases as the water content of the reaction medium is decreased. Thus, although it might appear obvious to try to operate the process of Paulik et al at minimal water concentration in order to reduce the cost of handling reaction product containing a substantial amount of water while still retaining enough water for adequate reaction rate, the requirement for appreciable water in order to maintain catalyst activity and stability works against this end.

Other reaction systems are known in the art in which an alcohol such as methanol or an ether such as dimethyl ether can be carbonylated to an acid or ester derivative using special solvents such as aryl esters of the acid under substantially anhydrous reaction conditions. The product acid itself can be a component of the solvent system. Such a process is disclosed in U.S. Pat. No. 4,212,989 issued July 15, 1980 to Isshiki et al, with the catalytic metal being a member of the group consisting of rhodium, palladium, iridium, platinum, ruthenium, osmium, cobalt, iron, and nickel. A somewhat related patent is U.S. Pat. No. 4,336,399 to the same patentees, wherein a nickel-based catalyst system is employed. Considering U.S. Pat. No. 4,212,989 in particular, the relevance to the present invention is that the catalyst comprises both the catalytic metal, as exemplified by rhodium, along with what the patentees characterize as a promoter, such as the organic iodides employed by Paulik et al as well as what the patentees characterize as an organic accelerating agent. The accelerating agents include a wide range of organic compounds of trivalent nitrogen, phosphorus, arsenic, and antimony. Sufficient accelerator is used to form a stoichiometric coordination compound with the catalytic metal. Where the solvent consists solely of acetic acid, or acetic acid mixed with the feedstock methanol, only the catalyst promoter is employed (without the accelerating agent), and complete yield data are not set forth. It is stated, however, that in this instance "large quantities" of water and hydrogen iodide were found in the product, which was contrary to the intent of the patentees.

European published patent application No. 0,055,618 to Monsanto Company discloses carbonylation of an alcohol using a catalyst comprising rhodium and an iodide or bromine component wherein precipitation of the catalyst during carbon monoxide-deficient conditions is alleviated by adding any of several named stabilizers. A substantial quantity of water, of the order of 14–15 wt. %, was employed in the reaction medium. The stabilizers tested included simple iodide salts, but the more effective stabilizers appeared to be any of several types of specially-selected organic compounds. When an iodide salt is used as the stabilizer, the amount used is relatively small and the indication is that the primary criterion in selecting the concentration of iodide salt to be employed is the ratio of iodide to rhodium. That is, the patentees teach that it is generally preferred to have an excess of iodine over the amount of iodine which is present as a ligand with the rhodium component of the catalyst. Generally speaking the teaching of the patentees appears to be that iodide which is added as, for example, an iodide salt functions simply as a precursor component of the catalyst system. Where the patentees add hydrogen iodide, they regard it as a precursor of the promoter methyl iodide. There is no clear teaching that simple iodide ions as such are of any significance nor that it is desirable to have them present in substantial excess to increase the rate of the reaction. As a matter of fact Eby and Singleton [*Applied Industrial Catalysis,* Vol. 1, 275–296 (1983)] from Monsanto state that iodide salts of alkali metals are inactive as cocatalyst in the rhodium-catalyzed carbonylation of methanol.

Carbonylation of esters, such as methyl acetate, or ethers, such as dimethyl ether, to form a carboxylic acid anhydride such as acetic anhydride is disclosed in U.S Pat. No. 4,115,444 to Rizkalla and in European patent application No. 0,008,396 by Erpenbach et al and assigned to Hoechst. In both cases the catalyst system comprises rhodium, an iodide, and a trivalent nitrogen or phosphorus compound. Acetic acid can be a component of the reaction solvent system, but it is not the reaction product. Minor amounts of water are indicated to be acceptable to the extent that water is found in the commercially-available forms of the reactants. However, essentially dry conditions are to be maintained in these reaction systems.

U.S. Pat. No. 4,374,070 to Larkins et al teaches the preparation of acetic anhydride in a reaction medium which is, of course, anhydrous by carbonylating methyl acetate in the presence of rhodium, lithium, and an iodide compound. The lithium can be added as lithium iodide compound. Aside from the fact that the reaction is a different one from that with which the present invention is concerned, there is no teaching that it is important per se that the lithium be present in any particular form such as the iodide. There is no teaching that iodide ions as such are significant. This patent further discloses feeding 2 to 7 volume % hydrogen to the reactor to suppress tar formation and significantly increase the reaction rate in terms of methyl acetate conversion as well as acetic anhydride production.

On the other hand, in an article in *Chem Tech,* Vol. 1, Oct. 1971, pages 600–605, James F. Roth et al describe the results of many experiments conducted on the carbonylation of methanol to acetic acid apparently utilizing the Monsanto commercial process. This process is essentially that described in previously mentioned U.S. Pat. No. 3,769,329 (Paulik et al). Among the results found was that the addition of hydrogen did not affect reaction rate. As hydrogen exerted no ill effect on the product composition, hydrogen was characterized as an inert diluent. Such finding is consistent with the disclosure in U.S. Pat. No. 3,769,329 wherein it is disclosed that carbon monoxide streams containing inert impurities such as hydrogen, carbon dioxide, methane, nitrogen, noble gases, water, and light paraffinic hydrocarbons may be employed from an available plant gas stream with no adverse effect, although in such cases total reactor pressure will have to be increased to maintain a desired carbon monoxide partial pressure. Concentrations of carbon monoxide in the feed gas mixture can be from 1 vol. percent to 100 vol. percent. Moreover, Paulik et al disclose that the rhodium-halogen catalyzed carbonylation process is readily adaptable to purifying hydrogen streams of carbon monoxide impurities since the carbon monoxide in such a gas mixture readily undergoes reaction with an alcohol, for example butyl alcohol to yield pentanoic acid.

Another patent describing the use of hydrogen in carbonylation reactions is U.K. patent application GB 2,155,929, published Oct. 2, 1985. In this particular patent, a process for producing acetic anhydride by the carbonylation of methyl acetate comprises separating the reaction mixture formed in the carbonylation reaction step into a volatile component and a rhodium-containing catalyst solution, heat treating the separated catalyst solution in the presence of a hydrogen-containing gas, and recirculating the hydrogenated catalyst solution to the carbonylation reaction step. It has been found that the activity of the rhodium catalyst was recovered. The patent specification states that the invention is also useful for the carbonylation of methanol.

In Japanese application 82-163034, Early Disclosure No. 59-53440, published Mar. 28, 1985 is disclosed a process for simultaneously preparing acetic anhydride and acetic acid comprising carbonylating a mixture of methyl acetate and methanol in a liquid phase containing the presence of rhodium, a 3-substituted phosphine, chromium or zirconium, and an iodine compound. The carbon monoxide feed may contain 1 to 10 mol % $H_2$ to affect the selectivity of reaction and the life of catalytic activity. The molar ratio of methyl acetate to methanol in the mixture is disclosed as ranging from ⅓ to 3/1. A methyl acetate-methanol mixture containing an excessive amount of methanol used as feed is to be avoided since the amount of produced acetic anhydride is small and thus, would deviate from the object of the invention as well as be troublesome to separate and obtain acetic anhydride from the reaction mixture. A methyl acetate-methanol mixture containing water, if in a small amount, is disclosed as being useful as the feed.

A similar process for the anhydrous co-production of acetic acid and acetic anhydride is disclosed in European patent application 170,965, published Feb. 12, 1986 and assigned to Hoechst A.G. A catalyst system comprising rhodium and a phsophonium compound is used along with an organic iodide. Hydrogen can be added to the reaction medium in amounts of about 10 volume percent.

European patent applications 144,935 and 144,936, published June 19, 1985 and assigned to Union Carbide Corporation, disclose processes for the production of carboxylic acids from alcohols such as the production of acetic acid from methanol. The two European patent applications disclose processes for the production of acetic acid by the catalytic reaction of methanol and carbon monoxide in contact with methyl acetate and a homogeneous catalyst system containing rhodium metal and lithium iodide, and rhodium metal and a mixture of lithium iodide and methyl iodide, respectively. Both of the published European patent applications state that the invention disclosed therein does not require the use of acidic halogen promoters as it employes the alkali metal halide lithium iodide, nor does the invention require the presence of water or use of large quantities of methyl iodide to give selectivity to acetic acid as taught in U.S. Pat. No. 3,769,329 to Monsanto. Other than this broad statement, the published European patent applications to Union Carbide are silent on the effect of water on reaction rate.

An improvement in the prior-art process for the carbonylation of an alcohol to produce the carboxylic acid having one carbon atom more than the alcohol in the presence of a rhodium catalyst is disclosed in copending, commonly assigned application U.S. Ser. No. 699,525, filed Feb. 8, 1985, now abandoned and European patent application 161,874; published Nov. 21, 1985. As disclosed therein acetic acid (HOAc) is produced from methanol (MeOH) in a reaction medium comprising methyl acetate (MeOAc), methyl halide, especially methyl iodide, (MeI), and rhodium present in a catalytically-effective concentration. The invention therein resides primarily in the discovery that catalyst stability and the productivity of the carbonylation reactor can be maintained at surprisingly high levels, even at very low water concentrations, i.e. 4 wt. % or less, in the reaction medium (despite the general industrial practice of maintaining approximately 14 wt. % or 15 wt. % water) by maintaining in the reaction medium, along with a catalytically-effective amount of rhodium, at least a finite concentration of water, methyl acetate and methyl iodide, and a specified concentration of iodide ions over and above the iodide content which is present as methyl iodide or other organic iodide. The iodide ion is present as a simple salt, with lithium iodide being preferred. The application teaches that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt. %, so low that it can broadly be defined simply as "a finite concentration" of water. Furthermore, the reaction medium employed improves the stability of the rhodium catalyst, i.e. resistance to catalyst precipitation, especially during the product-recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Ser. No. 699,525 is herein incorporated by reference.

In summary, with exception to the improved carbonylation process as described in commonly assigned U.S. Ser. No. 699,525, current technology in the field of carbonylating an alcohol such as methanol to form a carboxylic acid such as acetic acid lacks a simple method for maintaining a highly stable catalyst system and for attaining industrially attractive conversion rates at conditions of low water content in the liquid reaction medium whereby the expense and capital investment costs of recovering the acid product with a very low water content can be minimized. Even with the improved carbonylation process as described in commonly assigned U.S. Ser. No. 699,525, there is still a need to increase reaction rates.

It is, accordingly, an object of the present invention to provide a reaction system with which an alcohol, as exemplified by methanol, can be carbonylated to a carboxylic acid derivative such as acetic acid at an increased carbonylation rate above that which is disclosed in commonly assigned U.S. Ser. No. 699,525 using a liquid reaction medium having a lower water content than heretofore considered feasible. It is another object to provide a catalyst system which, regardless of the water content of the reaction medium, will be of improved stability, i.e., more resistant to precipitation of solid catalyst therefrom. It is also a related object to provide a catalyst system characterized by a substantial reduction in the undesired formation of by-product propionic acid and carbon dioxide as compared with high water systems used in the prior art. Other objects will be apparent from the following description.

SUMMARY OF THE INVENTION

Broadly, the invention is an improvement in the rhodium-catalyzed carbonylation of an alcohol to produce a carboxylic acid having one carbon atom more than the alcohol. In particular, the invention is directed to producing acetic acid by the carbonylation of methanol. It has now been discovered that the presence of hydrogen in the reaction medium for the rhodium-catalyzed carbonylation of alcohols to carboxylic acid has a beneficial effect on reaction rates. This effect is particularly found when the reaction medium contains very low water concentrations of below about 14 wt. %.

In accordance with the present invention a saturated alcohol is converted to a carboxylic acid by reacting the alcohol in the liquid phase with carbon monoxide in the presence of a reaction medium comprising a rhodium catalyst, the ester of the alcohol being carbonylated with the acid product of the carbonylation reaction, a halide derivative of the hydrocarbon corresponding to the alcohol, especially the iodide, and an iodide ion which is present in amounts over and above the iodide which is present as the hydrocarbon halide, and where the water concentration is below about 14 wt. % and where the reaction medium further contains hydrogen in an amount sufficient to provide a hydrogen partial pressure of at least about 4.0 psi in the reactor. The hydrogen is preferably provided in the reactor by co-feeding hydrogen with the carbon monoxide reactant.

BRIEF DESCRIPTION OF THE DRAWINGS

FIGS. 3–27 graphically illustrate interactions among the several reaction medium components in comparative examples in which the hydrogen partial pressure was maintained below 4 psi.

DESCRIPTION OF THE PREFERRED EMBODIMENTS

Figure 1:
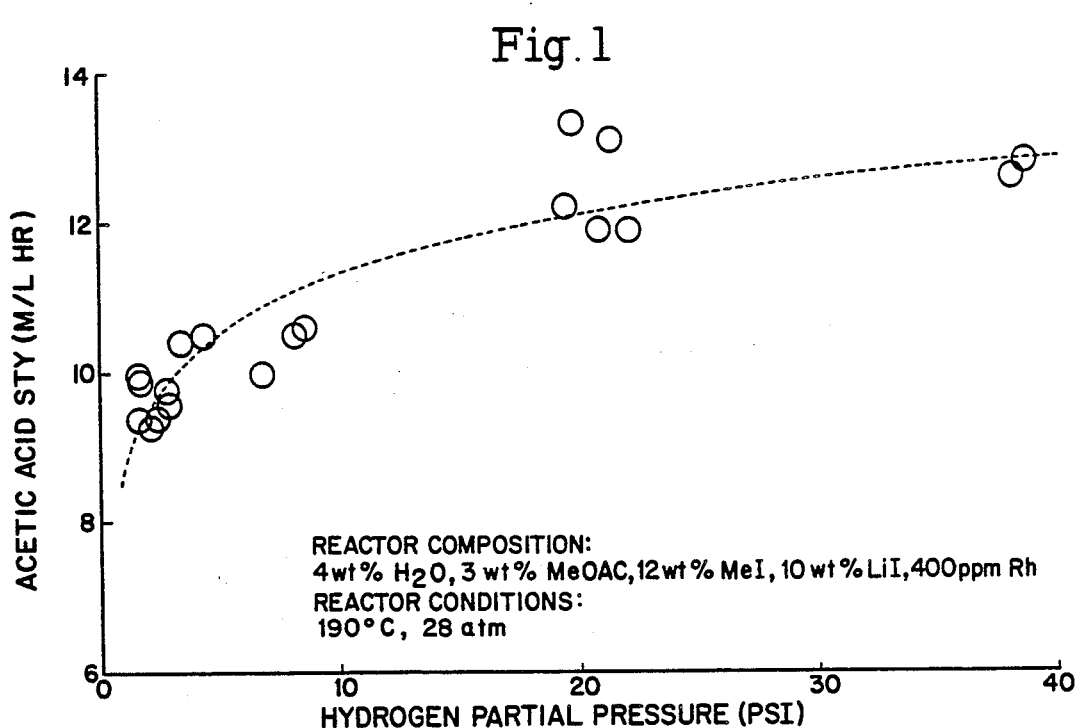
FIGS. 1 and 2 graphically illustrate interactions among the several reaction medium components in an example which forms the basis of the present invention.

The following description is directed to the carbonylation of methanol to produce acetic acid. However, the technology is applicable to the carbonylation of higher homologues of methanol to form acids which are the higher homologues of acetic acid.

There are two criteria which need to be satisfied to maintain optimal performance of a reaction system for the rhodium-catalyst carbonylation of methanol to acetic acid. This is over and above the maintenance of a stable catalyst system from which the rhodium catalyst does not precipitate during the course of product recovery. First, it is desired to maintain a high productivity in the carbonylation reactor itself, as measured by the quantity of acetic acid formed per unit time per unit volume or weight of liquid reaction medium contained in the reactor. This might be termed "reactor productivity" or "reactor space-time yield". Here again the art as it presently exists recognizes the need to maintain reactor productivity although it has not taught the presently-described methods for attaining this end.

Second, the present process improvement contemplates the maintenance of optimal productivity, as measured by the ultimately-recovered concentrated acetic acid in the combined system including both the carbonylation reactor and the product recovery system. Although the details of the product recovery system are not directly relevant to the present disclosure, it will be recognized by anyone skilled in the art that water is an undesirable component of the crude acetic acid and that the more water there is in this stream the greater will be the operating costs and required capital investment in the product recovery-purification system. Thus, there is also a "system productivity" to be considered in addition to the "reaction productivity", with the "system productivity" depending upon the degree to which water is kept out of the residue of the crude product stream. The dryer this stream is, the higher will be the over-all system productivity so long as reaction productivity is maintained.

The present process improvement is directed at maintaining both an optimal reactor productivity and also an optimal over-all system productivity. Fundamentally, the current state of the art seem to be resigned to accepting a relatively high water content in the liquid reaction medium with a resulting undesirably high water content in the crude acetic acid initially recovered from the reaction and primary product recovery system.

As previously explained, the rate of the carbonylation reaction according to the present state of the art has been highly dependent on water concentration in the reaction medium as taught by U.S. Pat. No. 3,769,329; EP0,055,618; and Hjortkjaer and Jensen (1977). That is, as the water concentration is reduced below about 14–15 wt. % water, the rate of reaction declines. The catalyst also becomes more susceptible to inactivation and precipitation when it is present in process streams of low carbon monoxide partial pressures. It has now been discovered, however, that by utilizing a novel reaction medium increased acetic acid-production capacity can be achieved at water concentrations below about 14 wt. % (at water contents above about 14 wt. %, the reaction rate is not particularly dependent on water concentration).

For the purposes of this invention, the catalyst which is employed includes a rhodium component and a halogen promoter in which the halogen is either bromine or iodine. Generally, the rhodium component of the catalyst system of the present invention is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium.

The rhodium component of the catalyst system in the present invention may be provided by introducing into the reaction zone rhodium in the form of rhodium metal, rhodium salts and oxides, organic rhodium compounds, coordination compounds of rhodium, and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the process of this invention comprises the carboxylic acid product. Thus, in the carbonylation of methanol to acetic acid, the preferred solvent is acetic acid.

Water is also added to the reaction medium, but, at concentrations well below what has heretofore been thought practical for achieving sufficient reaction rates. It is known that in rhodium-catalyzed carbonylation reactions of the type set forth in this invention, the addition of water exerts a beneficial effect upon the reaction rate (U.S Pat. No. 3,769,329). Thus, commercial operations run at water concentrations of at least 14 wt. % (EP 0,055,618). Accordingly, it is quite unexpected that reaction rates substantially equal to and above reaction rates obtained with such high levels of water concentration can be achieved with water concentrations below 14 wt. % and as low as 0.1 wt. %. In accordance with the present invention, the desired reaction rates are obtained even at low water concentrations by including in the reaction medium an ester which corresponds to the alcohol being carbonylated and the acid product of the carbonylation reaction and an additional iodide ion which is over and above the iodide which is present as a catalyst promoter such as methyl iodide or other organic iodide. Thus, in the carbonylation of methanol to acetic acid, the ester is methyl acetate and the additional iodide promoter is an iodide salt, with lithium iodide being preferred.

It has been found that under low water concentrations, methyl acetate and lithium iodide act as rate promoters only when relatively high concentrations of each of these components are present and that the promotion is higher when both of these components are present simultaneously. This has not been recognized in the prior art previous to disclosure of commonly assigned U.S. Ser. No. 699,525. The concentration of lithium iodide used in the reaction medium of the present invention is believed to be quite high as compared with what little prior art there is dealing with the use of halide salts in reaction systems of this sort.

It has now also been discovered that in reaction mediums having a methyl acetate concentration of greater than about 2 wt. %, lithium iodide is necessary not only to increase the reaction rate but also to stabilize the rhodium catalyst due to the deleterious effect of high methyl acetate concentrations on its stability, even at high water concentrations.

It has now been determined for the various reaction components that the amounts of water, iodide salt, methyl acetate, and methyl iodide as set forth in the following Table I, in which there is set forth both a broad range and a preferred, or optimal, range, are necessary for obtaining both catalyst stabilization and reaction rate enhancement. The "preferred" range is that which is preferred from the standpoint of optimal performance of the entire system including the primary product recovery system as explained hereinabove. It will be seen that the recommended concentrations are the same for both stabilization and also rate enhancement with one exception: the exception is that the "preferred" range for methyl acetate is 0.5–5 wt. % for catalyst stabilization whereas it is 2–5 wt. % for optimal rate enhancement. Broadly of course, this means that in either case a range between 0.5 wt. % and 5 wt. % would be satisfactory, but that, depending upon whether it is catalyst stabilization or maximal rate enhancement that one aims to maximize in a given plant operating situation, the bottom end of the desired methyl acetate range is slightly higher when maximal rate enhancement is being sought.

TABLE I

|  | Stabilization | | Rate Enhancement | |
| --- | --- | --- | --- | --- |
|  | Broad wt. % | Preferred wt. % | Broad wt. % | Preferred wt. % |
| $H_2O$ | 0.1–20 | 1–4 | 0.1–20 | 1–4 |
| Inorganic Iodide (as LiI) | 2–20 | 10–20 | 2–20 | 10–20 |
| MeOAc | 0.5–30 | 0.5–5 | 0.5–30 | 2–5 |
| MeI | 5–20 | 12–16 | 5–20 | 12–16 |
| HOAc | Balance | Balance | Balance | Balance |
| Rh (ppm) | 200–1000 | 300–600 | 200–1000 | 300–600 |

An important addition to the reaction medium and the subject matter of the present invention is a finite concentration of hydrogen. While the prior art was concerned that hydrogen impurities in the carbon monoxide feedstream may be detrimental and discovered otherwise, characterizing hydrogen as a mere inert diluent, it has now been found that when utilizing the reaction medium of the present invention wherein the water content is well below commercial practice, hydrogen in the reactor is not merely an inert gas, but actually improves the reaction rate for the production of carboxylic acid. To achieve the improved reaction rates for the formation of the desired carboxylic acid, the carbonylation reactor should contain a hydrogen partial pressure of at least about 4 psi at the reactor conditions of 150°–250° C. and 15 to 40 atmospheres total reaction pressure. Preferably, the hydrogen partial pressure will be at least about 10 psi, more preferably, at least about 20 psi with even $H_2$ partial pressures as high as 40 psi providing rate enhancement. Higher partial pressures of $H_2$ are also contemplated by the invention although $H_2$ partial pressures above 150 psi are not believed to substantially improve reaction rates. All pressures as herein stated refer to absolute pressure.

The hydrogen in the carbonylation reactor is provided by cofeeding small amounts of hydrogen with the carbon monoxide feed. To achieve the desired hydrogen partial pressures in the carbonylation reactor, the requirements of hydrogen in the feed are quite small. For example, to maintain a partial pressure of hydrogen in the reactor of from about 4 psi to about 40 psi, with normal venting of the inert reaction gases, such as carbon dioxide and nitrogen, feed concentrations of hydrogen of between about 0.3 mol % to 2.5 mol % are all that is required. Hydrogen feed concentrations of from about 0.3 mol % to 10 mol % are useful to provide sufficient hydrogen in the reaction. Preferably from about 1 mol % to 5 mol % $H_2$ in the feed stream provides desired reaction rate enhancement for forming the carboxylic acid product. It can readily been seen that controlling the venting of product gases which will include co-fed hydrogen as well as hydrogen formed during reaction can affect the hydrogen partial pressure in the reactor. It is preferred to control the hydrogen partial pressure by including hydrogen in the feed stream as opposed to merely reducing the steady state venting of product gases inasmuch as the steady state concentration of inert gaseous byproducts may build up in the reactor thus reducing the reactor carbon monoxide partial pressure to where the reaction becomes dependent on the reactor carbon monoxide partial pressure.

What has been found is that the addition of hydrogen to the carbonylation reactor yields increased rates in the production of the carboxylic acid and, thus, in the carbonylation of methanol to acetic acid, yields increased rates of production of the acetic acid compared to the carbonylation of methanol wherein higher levels of hydrogen are not expressly maintained. This is contrary to what has been recognized in the art in which hydrogen was characterized as an inert diluent only with no adverse effect on reaction rates. The difference found herein concerning the effect hydrogen has on reaction rates is believed to be the result of the use of reaction mediums which contain low amounts of water, that is water contents below about 14 wt. %, and preferably between about 1 and 4 wt. % of the reaction medium. Further, not only are the rates of production of acetic acid increased, the rate of carbon dioxide formation is drastically reduced by providing a hydrogen partial pressure in the carbonylation reactor of at least 4.0 psi and, in particular, when the hydrogen partial pressure approaches about 20 psi.

It is believed that the increase in reaction rates, especially for the production of acetic acid, found by increasing the hydrogen partial pressure in the carbonylation reactor involves shifts in the $Rh^I/Rh^{III}$ equilibrium involved in the water gas shift reaction:

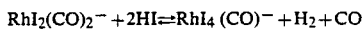

$$RhI_2(CO)_2^- + 2HI \rightleftharpoons RhI_4(CO)^- + H_2 + CO$$

Therefore, as the hydrogen partial pressure increases the $Rh^I/Rh^{III}$ ratio increases and consequently the carbonylation rate increases and the water gas shift reaction decreases as shown by the increased rates of acetic acid and the decreased carbon dioxide product formation.

Useful feedstocks which can be carbonylated according to the teachings of the present invention include alkanols containing 1–20 carbon atoms. Preferred feedstocks are alkanols containing 1–10 carbon atoms, and more preferred are alkanols of 1–5 carbon atoms. Methanol is the particularly preferred feed and is converted to acetic acid in accordance with the teachings of the present invention.

In accordance with the present invention, the carbonylation reaction may be carried out by intimately contacting the above defined feed alcohol, which is in the liquid phase, with gaseous carbon monoxide bubbled through a liquid reaction medium containing the rhodium catalyst, halogen-containing promoting component, alkyl ester, and additional soluble iodide salt promoter, at conditions of temperature and pressure suitable to form the carbonylation product. Thus, if the feed is methanol, the halogen-containing promoting component will comprise methyl iodide, the alkyl ester will comprise methyl acetate and the iodide salt will comprise any of several soluble iodide salts which are useful. It will be recognized that it is the concentration of iodide ion in this catalyst system that is important and not the cation associated with the iodide, and that at a given molar concentration of iodide the nature of the cation is not as significant as the effect of the iodide concentration. Any metal iodide salt, or any iodide salt of any organic cation, can be used provided that the salt is sufficiently soluble in the reaction medium to provide the desired level of the iodide. The iodide salt can be a quaternary salt of an organic cation or the iodide salt of an inorganic cation, preferably it is an iodide salt of a member of the group consisting of the metals of Group Ia and Group IIa of the periodic table as set forth in the "Handbook of Chemistry and Physics" published by CRC Press, Cleveland, Ohio 1975–76 (56th edition). In particular, alkali metal iodides are useful, with lithium iodide being preferred.

The reaction temperature will be approximately 150°–250° C., with the temperature range of about 180°–220° C. being the preferred range. The carbon monoxide partial pressure in the reactor can vary widely but is typically about 2–30 atmospheres, and preferably, about 4–15 atmospheres. Because of the partial pressure of by-products and the vapor pressure of the contained liquids, the total reactor pressure will range from about 15 to 40 atmospheres.

A reaction system which can be employed, within which the present improvement is used, comprises (a) a liquid-phase carbonylation reactor, (b) a so-called "flasher", and (c) a "methyl iodide-acetic acid splitter column". The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. Alternate distillation systems can be employed so long as they provide means for recovering the crude acetic acid and recycling to the reactor catalyst solution, methyl iodide, and methyl acetate. In the preferred process, a mixed carbon monoxide/hydrogen feed is continuously introduced into the carbonylation reactor just below the agitator which is used to stir the contents. The mixed gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. By controlling the venting of gases, it is also possible to control the hydrogen partial pressure in the reactor. The temperature of the reactor is controlled automatically, and the carbon monoxide/hydrogen feed is introduced at a rate sufficient to maintain the desired total reactor pressure.

Liquid product is drawn off from the carbonylation reactor at a rate sufficient to maintain a constant level therein and is introduced to the flasher at a point intermediate between the top and bottom thereof. In the flasher the catalyst solution is withdrawn as a base stream (predominantly acetic acid containing the rhodium and the iodide salt along with lesser quantities of methyl acetate, methyl iodide, and water), while the overhead of the flasher comprises largely the product acetic acid along with methyl iodide, methyl acetate, and water. A portion of the carbon monoxide and hydrogen along with gaseous by-products such as methane, hydrogen, and carbon dioxide exits the top of the flasher.

The product acetic acid drawn from the base of the methyl iodide-acetic acid splitter column (it can also be withdrawn as a side stream near the base) is then drawn off for final purification as desired by methods which are obvious to those skilled in the art and which are outside the scope of the present invention. The overhead from the methyl iodide-acetic acid splitter, comprising mainly methyl iodide and methyl acetate, is recycled to the carbonylation reactor along with fresh methyl iodide, the fresh methyl iodide being introduced at a rate sufficient to maintain in the carbonylation reactor the desired concentration of methyl iodide in the liquid reaction medium. The fresh methyl iodide is needed to compensate for losses of methyl iodide in the flasher and carbonylation reactor vent streams.

The primary reaction control method comprises continually analyzing the liquid contents of the reactor as well as the carbon monoxide and hydrogen content of the gas in the reactor vent and, on the basis of these analyses, controlling the flow of carbon monoxide, hydrogen, water, methanol, and methyl iodide to maintain the specified reaction medium composition. It should be further explained that the methanol addition to the carbonylation reactor is based not on an analysis of its contents for methanol but, rather, on analysis for methyl acetate content. Most of the methanol is converted almost immediately to methyl acetate when it enters the carbonylation reactor.

The process of the present invention may be operated either as a batch or as a continuous process. In batch operation the reactants are charged into the liquid catalyst solution, which is then subjected to the desired temperature and pressure conditions, after which the products are separated from the reaction mixture. In a continuous process which is described above, the catalyst system is maintained in liquid state, with the reactants being continuously supplied to the reaction zone containing the catalyst system at the desired temperature and pressure. The products are continuously withdrawn, as described above by withdrawing a portion of the solution containing the catalyst system, unreacted feed, equilibrium components, and the desired product. The desired product is then separated from such solution to permit recycling of the catalyst containing solution which includes unreacted feed and also equilibrium components.

EXAMPLES

Figure 2:
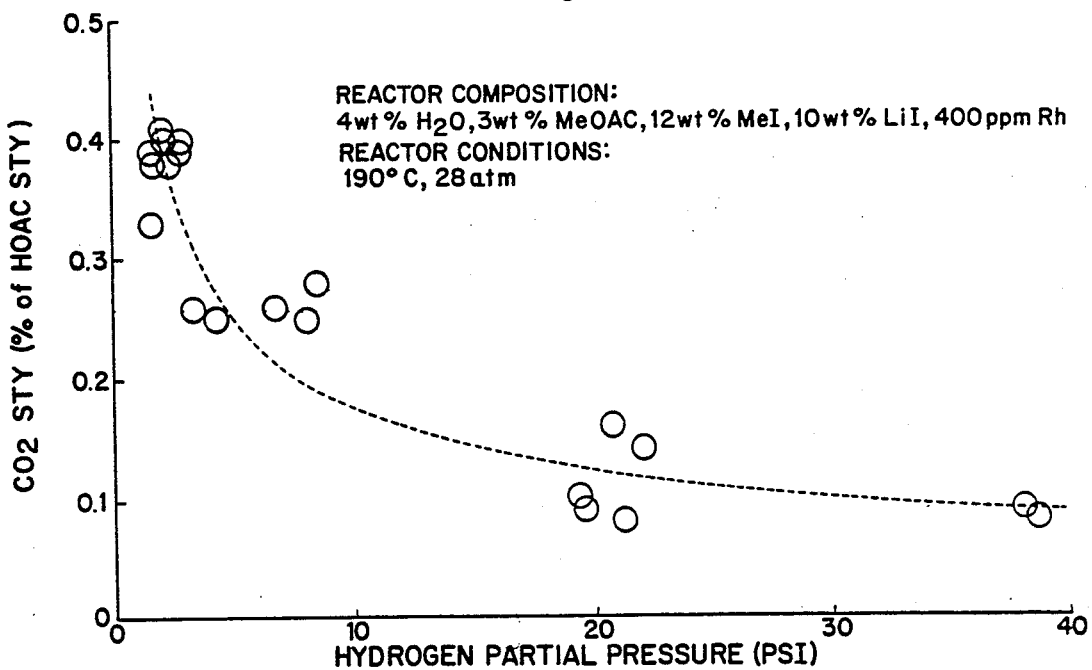

FIGS. 1 and 2 correspond to Example 1 wherein the effect of hydrogen partial pressure on reaction rates and byproduct formation was evaluated. FIGS. 3–27 correspond to comparative Examples 2–26 wherein experiments were conducted to illustrate the interaction of the reaction medium components in the carbonylation of methanol to acetic acid, in particular, the effect of iodide salt and methyl acetate on the carbonylation rate and catalyst stability. Comparative Examples 2–28 were run without hydrogen addition to the reactor. Some of these figures set forth the results of runs carried out in a batch autoclave, some present the results of runs carried out in a continuous pilot plant unit, and some are based on results obtained in a batch-operated glass vessel which was designed specifically to study catalyst stability.

The pilot plant was operated in the manner previously described in which there was included as a reactor a stirred autoclave followed by two product recovery system distillation steps. The process control scheme was as described also hereinabove. The reactor temperature in all cases was between about 190° C. and 195° C. The total reactor pressure was approximately 28 atmospheres, with the carbon monoxide partial pressure being approximately 8 to 12 atmospheres. In each case, the balance of the liquid reaction medium, not specifically listed in the corresponding figure was acetic acid. Because the reaction rate is directly proportional to the rhodium concentration, and to facilitate the comparison of the different runs, the STY in the runs set forth in the Figures have been normalized to 400 ppm rhodium unless otherwise indicated explicitly.

In the batch run, an autoclave of suitably corrosion-resistant metal was charged with rhodium triiodide (typically between 200 and 500 ppm rhodium content in the resulting mixture). The autoclave was sealed, pressured to approximately 28.2 atmospheres of carbon monoxide and the pressure checked at 25° C. After this the autoclave was slowly vented of its carbon monoxide content and then flushed two times by pressuring to 4.4 atmospheres with carbon monoxide followed by venting. The autoclave was then pressured to 11.2 atmospheres with carbon monoxide and heated to 185° C. to 190° C., after which the agitator with which the autoclave was provided was turned on. The autoclave was then further pressured with carbon monoxide to 28.4 atmospheres. The rate of reaction was determined by monitoring the amount of carbon monoxide consumed over a period of time while assuming that the ideal-gas law applied to carbon monoxide. Reaction rate was determined from plots of carbon monoxide uptake versus time, the resulting data then being converted to the carbonylation reaction rate assuming ideal gas behavior for the carbon monoxide.

The glass vessel was actually composed of two side-by-side vessels fabricated from glass pipe and designed to operate at pressures not to exceed about 2 atmospheres gauge at 150° C. To conduct a run, each of the glass vessels was initially charged with the desired weight of rhodium (as salts like RhI$_3$), HI, acetic acid, water, and stabilizer. Both vessels were then pressurized to about 1.8 atmospheres gauge with carbon monoxide and heated in an oil bath to 130° C. or 150° C. in order to dissolve the rhodium. Carbon monoxide was then bubbled into the solution at 47 ml per minute through a gas-inlet tube while the desired constant pressure was maintained by a back-pressure regulator system. After one hour, the rhodium salt was completely dissolved in the form of a rhodium carbonyl compound. The carbon monoxide was replaced by nitrogen and the total pressure was reduced to about 1 atmosphere gauge. This was considered the initial time of the stability experiment. Samples were removed through a sampling port, centrifuged for 5–10 minutes, and the clear centrifugate analyzed for soluble rhodium content.

EXAMPLE 1

The effect of hydrogen partial pressure on reaction rates and byproduct formation was evaluated in a continuously-operating apparatus comprising a stirred reactor from which the product was drawn off continuously for a workup in the manner previously described. The reaction medium comprised 4 wt. % water, 3 wt. % methyl acetate, 12 wt. % methyl iodide, and 10–12 wt. % LiI. The reaction was run at 190° C. and 400 psig pressure. Rhodium concentration varied between 335 ppm to about 800 ppm.

A base condition was run utilizing a pure carbon monoxide feed and three comparative runs containing 0.3 mol %, 1.3 mol % and 2.5 mol % hydrogen, respectively, in a mixed feed of CO and H$_2$. The results are shown in Table II.

As can be seen, even at very low concentrations of hydrogen in the feedstream the production of acetic acid is increased and importantly, the production of carbon dioxide is greatly reduced. As the reactor hydrogen partial pressure is increased over the range of 1 psi to 40 psi, the reaction rate for the production of acetic acid is greatly increased and CO$_2$ production is reduced.

FIGS. 1, and 2 graphically illustrate what is set forth in Table II for acetic acid production and CO$_2$ byproduct formation relative to the hydrogen partial pressure in the carbonylation reactor.

TABLE II *

| H$_2$ pp (psi) | HOAC STY (M/LHr) | CO$_2$ (% HOAC STY) | |
|---|---|---|---|
| 3.3 | 10.4 | 0.26 | 100 mol % CO Feed |
| 2.1 | 9.4 | 0.40 | |
| 2.1 | 9.3 | 0.41 | |
| 2.4 | 9.4 | 0.38 | |
| 2.9 | 9.6 | 0.40 | |
| 2.8 | 9.8 | 0.39 | |
| 1.6 | 9.4 | 0.39 | |
| 1.7 | 9.9 | 0.38 | |
| 1.6 | 10.0 | 0.33 | |
| 4.3 | 10.5 | 0.25 | 99.7 mol % CO + 0.3 mol % H$_2$ Feed |
| 6.7 | 10.0 | 0.26 | |
| 8.5 | 10.6 | 0.28 | |
| 8.1 | 10.5 | 0.25 | |
| 19.4 | 12.2 | 0.10 | 98.7 mol % CO + 1.3 mol % H$_2$ Feed |
| 21.3 | 13.1 | 0.08 | |
| 19.7 | 13.3 | 0.09 | |
| 20.8 | 11.9 | 0.16 | 97.5 mol % CO + 2.5 mol % H$_2$ Feed |
| 22.1 | 11.9 | 0.14 | |
| 38.7 | 12.8 | 0.08 | |
| 38.1 | 12.6 | 0.09 | |

* Reactor composition: 4 wt. % H$_2$O, 3 wt. % MeOAC, 12 wt. % MeI, 10 wt. % LiI, 400 ppm Rh
Reactor conditions: 190 deg C., 28 atm Total Pressure

EXAMPLES 2-26

These comparative Examples are the product of experiments which were conducted to illustrate the interaction of the reaction medium components in the carbonylation of methanol to acetic acid. In these comparative Examples, hydrogen partial pressures below about 3 psi were maintained in the carbonylation reactor inasmuch as hydrogen was not co-fed with the carbon monoxide feed.

Figure 3:
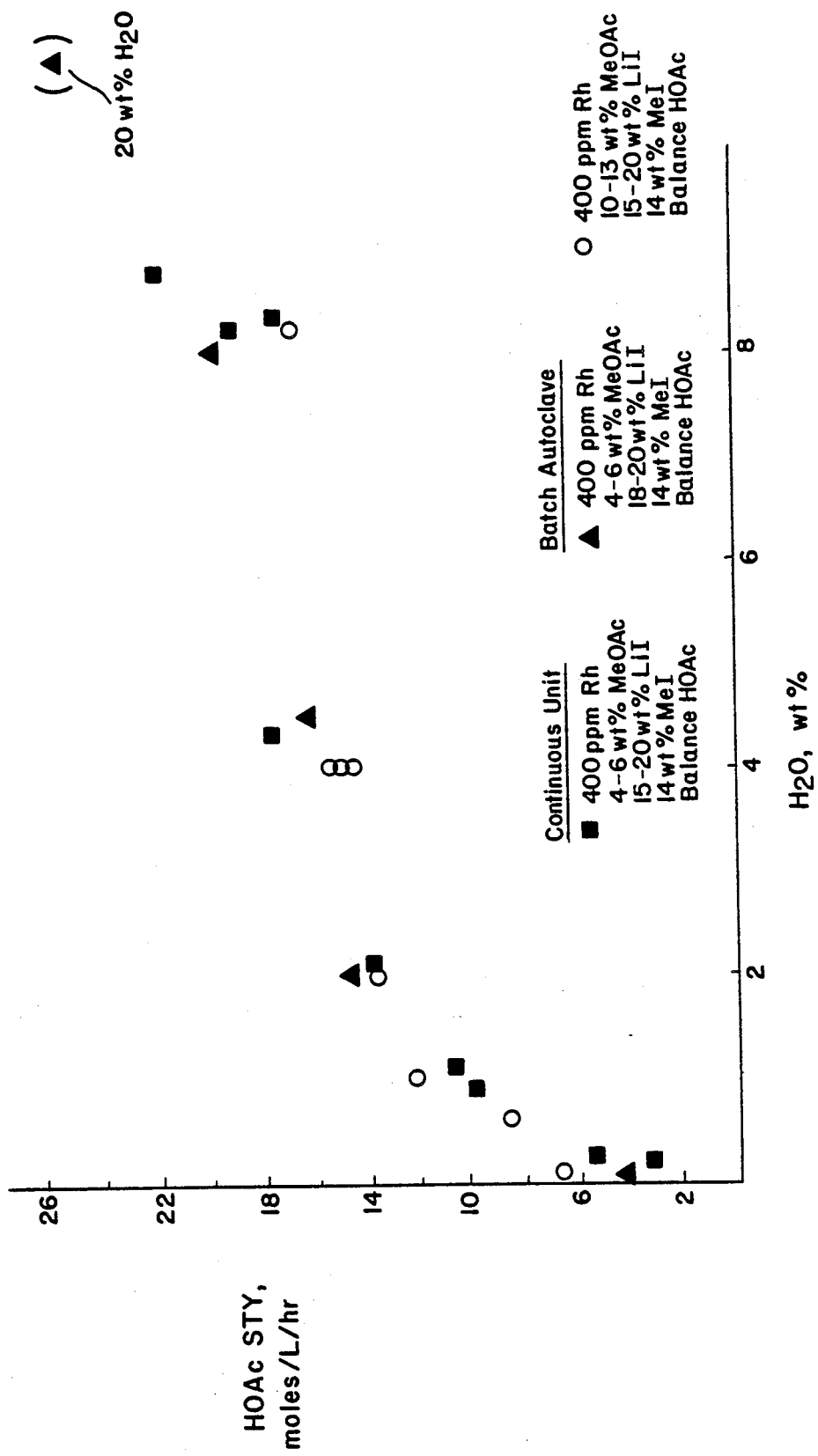
Figure 4:
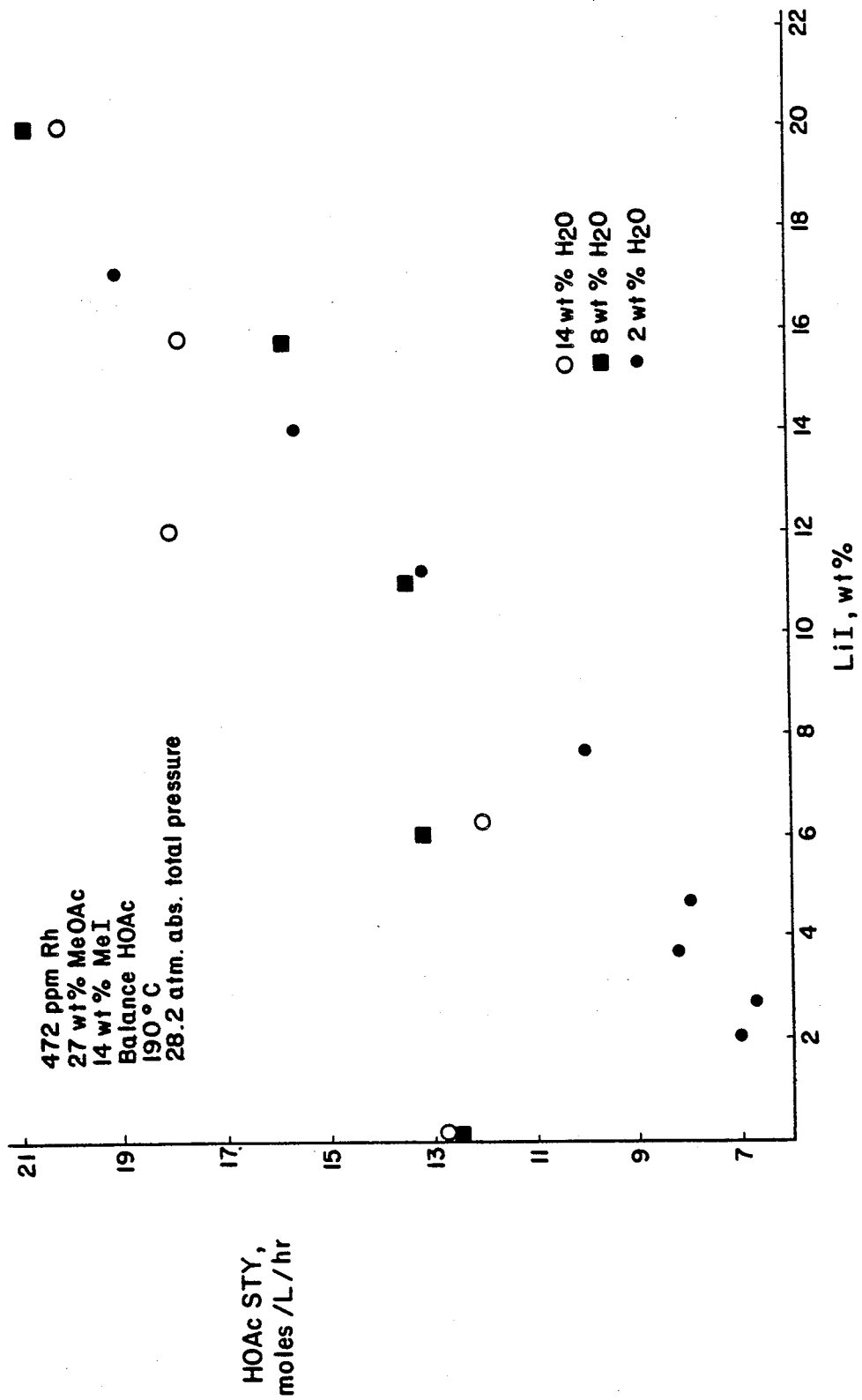

Turning now to the information set forth in the drawings and considering the drawings in numerical order:

FIGS. 3 through 11 show the results of batch experiments. FIG. 3 illustrates that reducing the water content of the reaction system reduces the reaction space-time yield, but that with high lithium iodide in the reaction medium along with high methyl acetate and methyl iodide, good carbonylation rates can be obtained at surprisingly low water concentrations. It also shows the agreement of data obtained in batch autoclave and the continuous unit. FIG. 4 illustrates that space-time yield increases with increasing lithium iodide concentration. Although there is some scatter in the data especially at high water concentration, it is also indicated that increasing the lithium iodide concentration mitigates what would otherwise be the adverse effect on reaction rate of reducing the water concentration. The effect of iodide at low water (2 wt. %) is very well defined and impressive.

Figure 5:
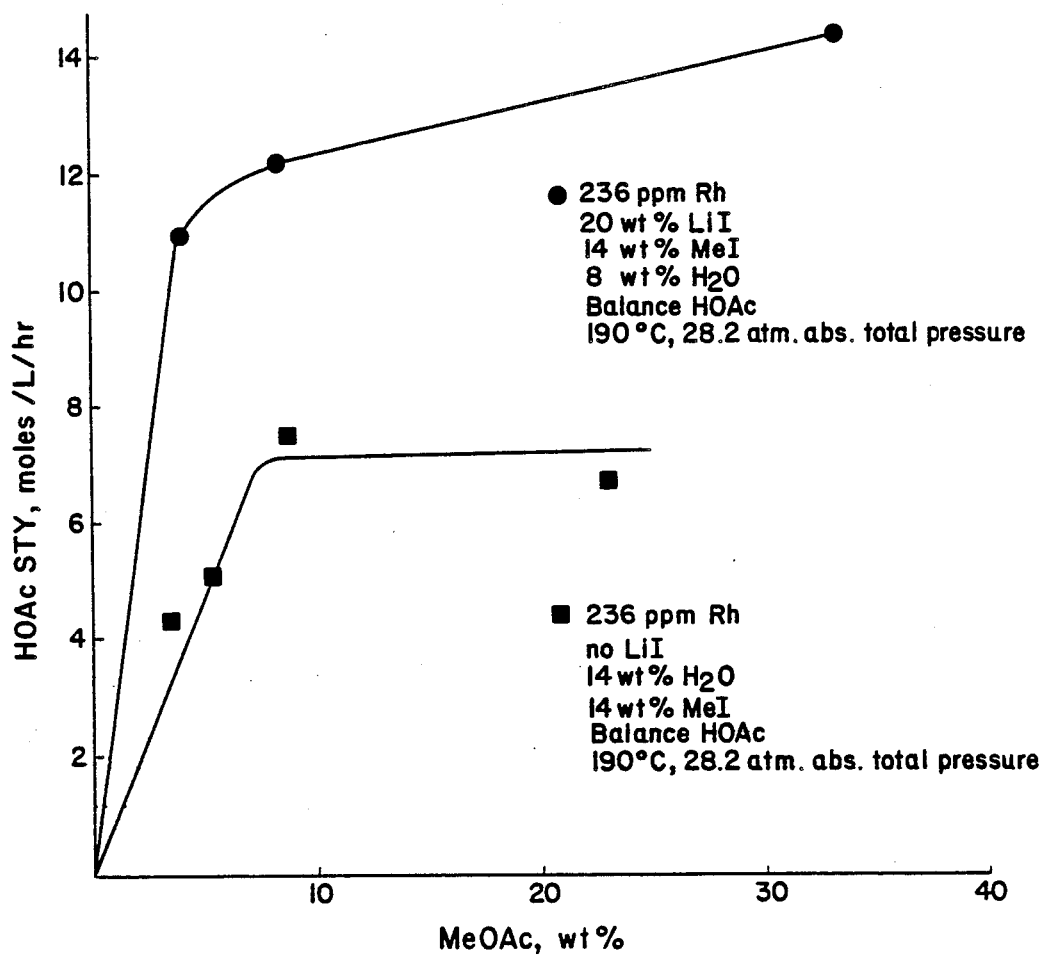

FIG. 5 demonstrates that the methyl acetate concentration is a significant factor and that it is inter-related with the employment of the lithium iodide stabilizer. Both with and without lithium iodide being present, increasing the methyl acetate concentration up to somewhat less than 10 wt. % increases the space-time yield, but with 20% lithium iodide being in the reaction medium the space-time yield at a given methyl acetate concentration is roughly double that observed when the lithium iodide is not present even at lower water concentration.

Figure 6:
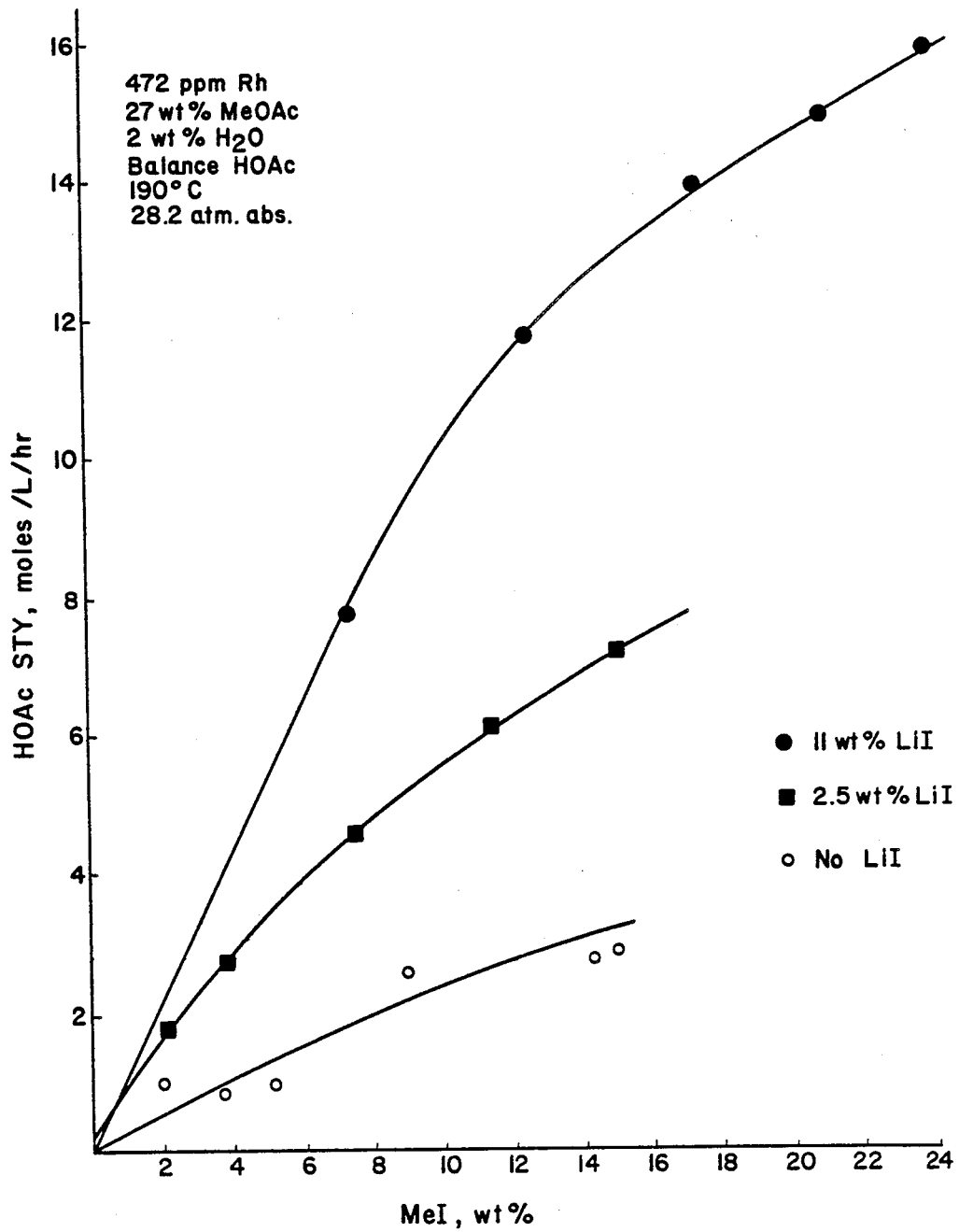

FIG. 6 illustrates the significance of methyl iodide concentration in the reaction medium with varying lithium iodide concentration. With no lithium iodide, space-time yield increases with increasing methyl iodide concentration but the space-time yields are relatively low. With 2.5 wt. % lithium iodide in the mixture the space-time yields are higher than with none, still, however, showing a methyl iodide dependency. With 11 wt. % lithium iodide the space-time yields are even higher, still showing an increase with increasing methyl iodide.

Figure 7:
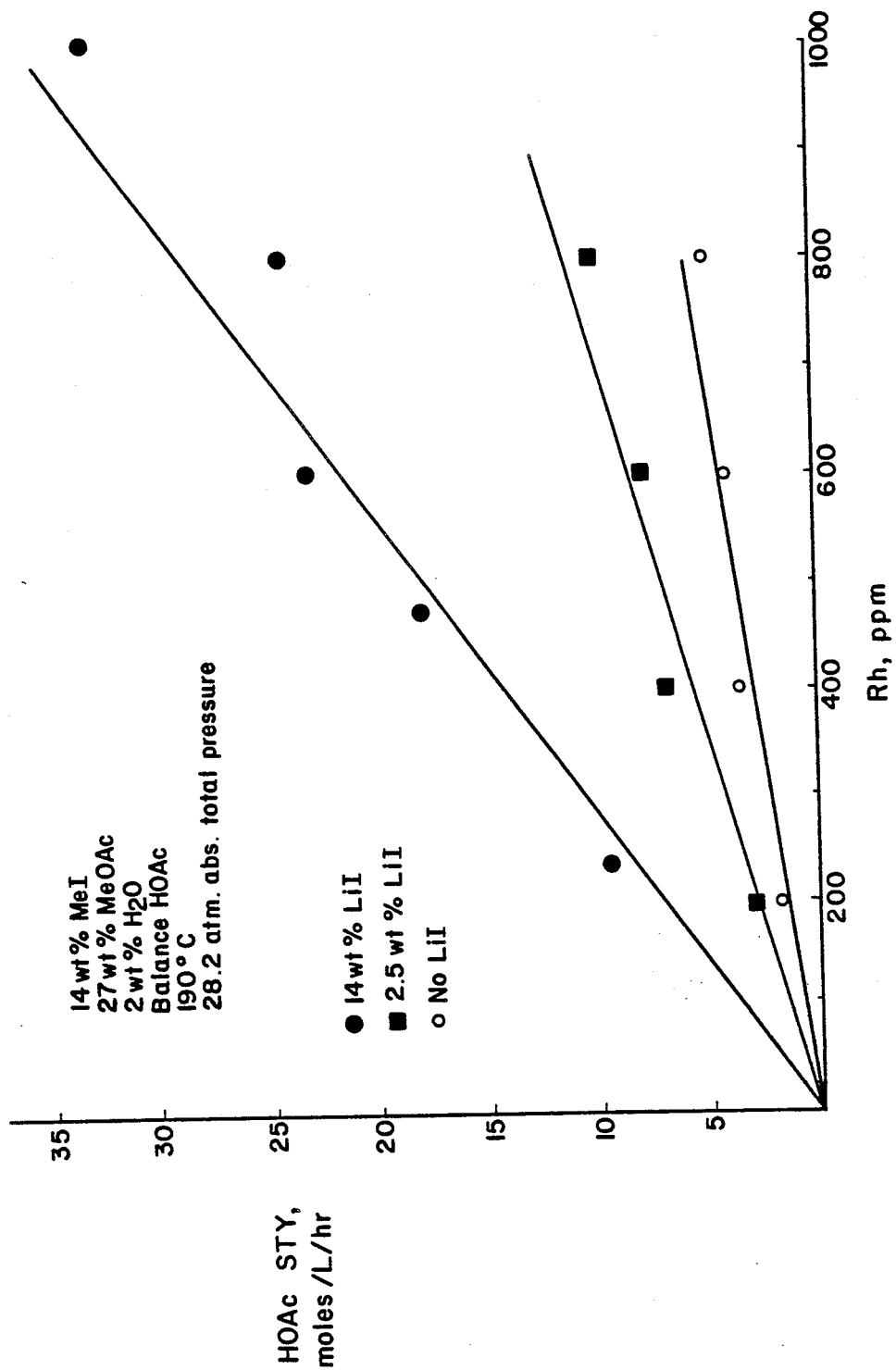

FIG. 7 demonstrates, not surprisingly, that the space-time yield increases with increasing rhodium concentration in the reaction medium. It is further demonstrated, however, that results are poorest when there is no lithium iodide present, better when there is 2.5 wt. % lithium iodide, and (within the range illustrated here) best when the lithium iodide concentration is 14 wt. %.

Figure 8:
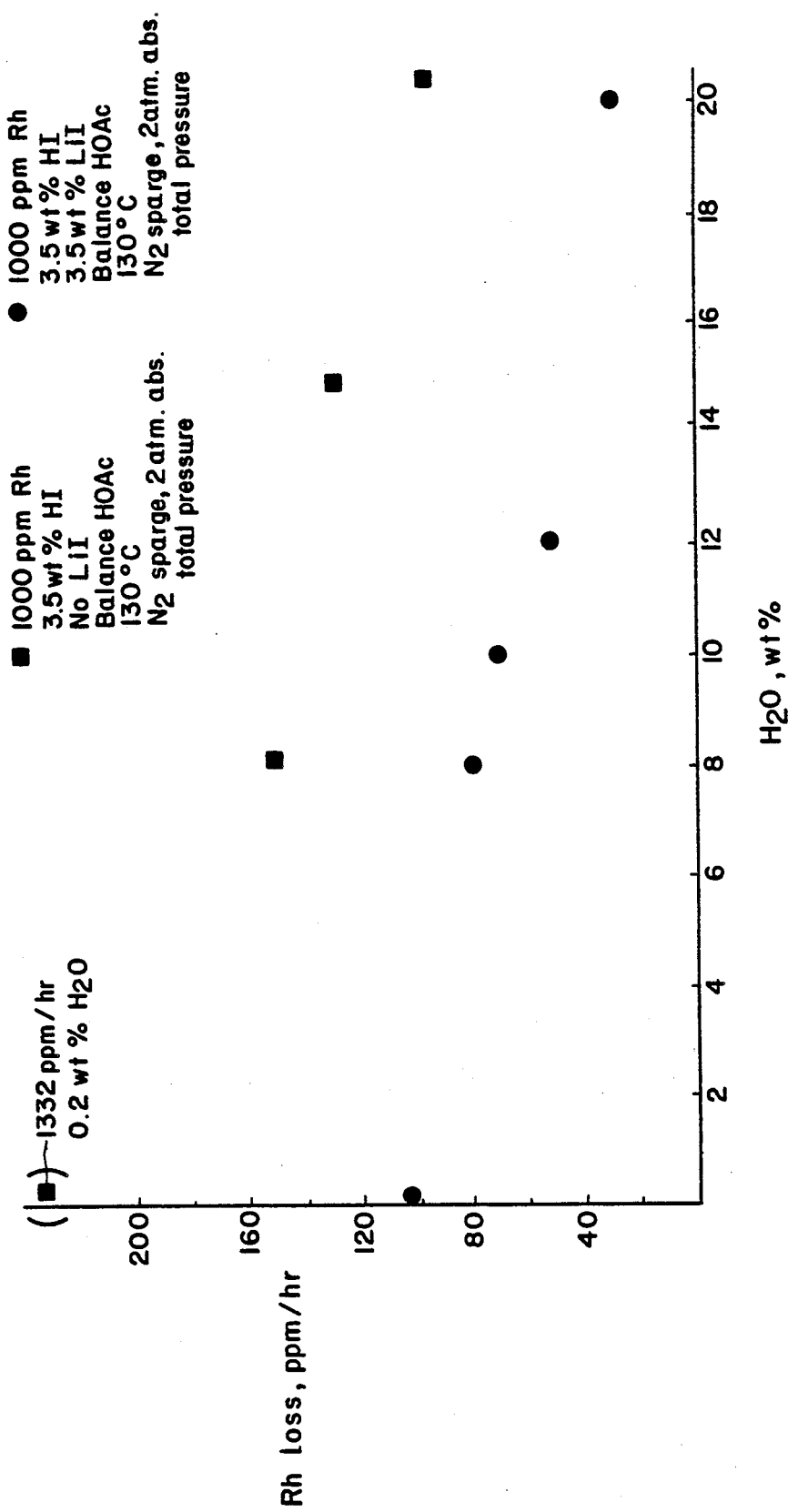
Figure 9:
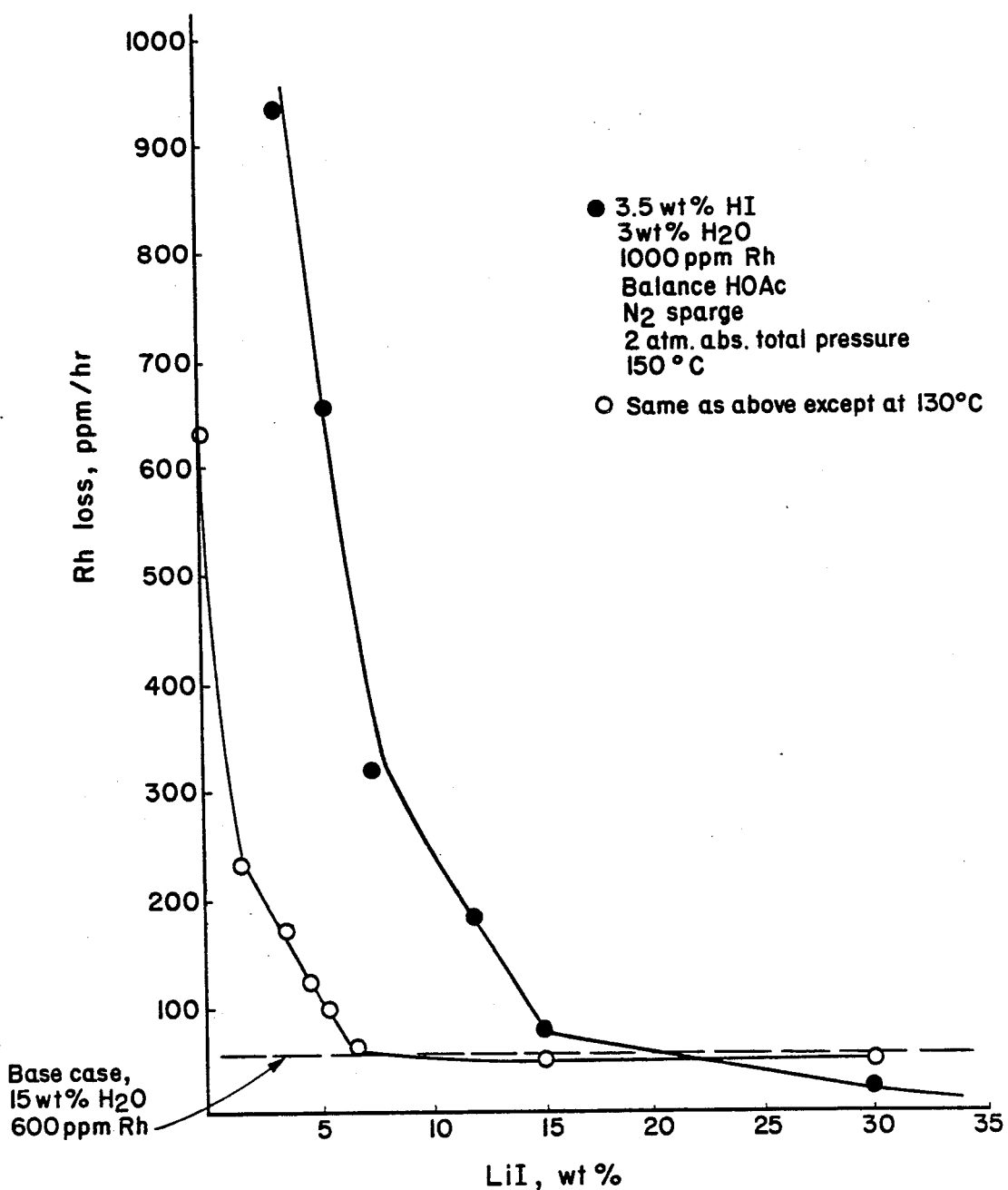
Figure 10:
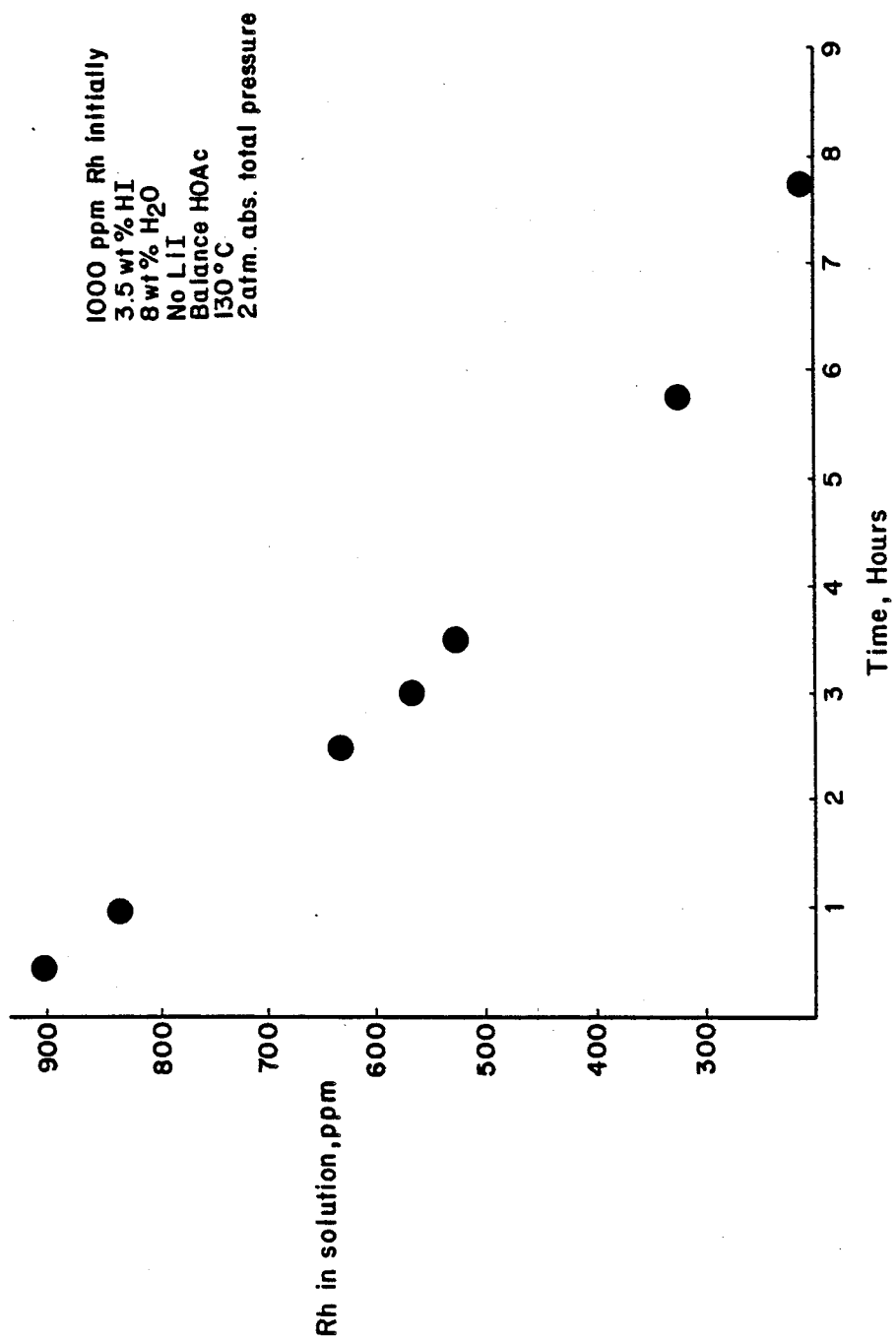

FIG. 8 illustrates that increasing water in the reaction medium decreases the rate of rhodium catalyst precipitation. Also illustrated in FIG. 8, an increase in iodide moiety by adding lithium iodide reduces the rate of rhodium precipitation out of the reaction medium at a given hydrogen iodide and water concentration. FIG. 9 illustrates the stabilizing effect of lithium iodide at low (3 wt. %) water concentration and at two temperatures (130° C. and 150° C.). At the lower temperature, roughly 6 wt. % lithium iodide results in catalyst stability as good as that obtained when using a reaction medium containing 15 wt. % water and needing no stabilizer. At the high temperature, about 15 wt. % lithium iodide is adequate. In FIG. 10 it is demonstrated that, in the absence of lithium iodide, very little rhodium remains in solution after 8 hours or less in a reaction medium of the composition described.

Figure 11:
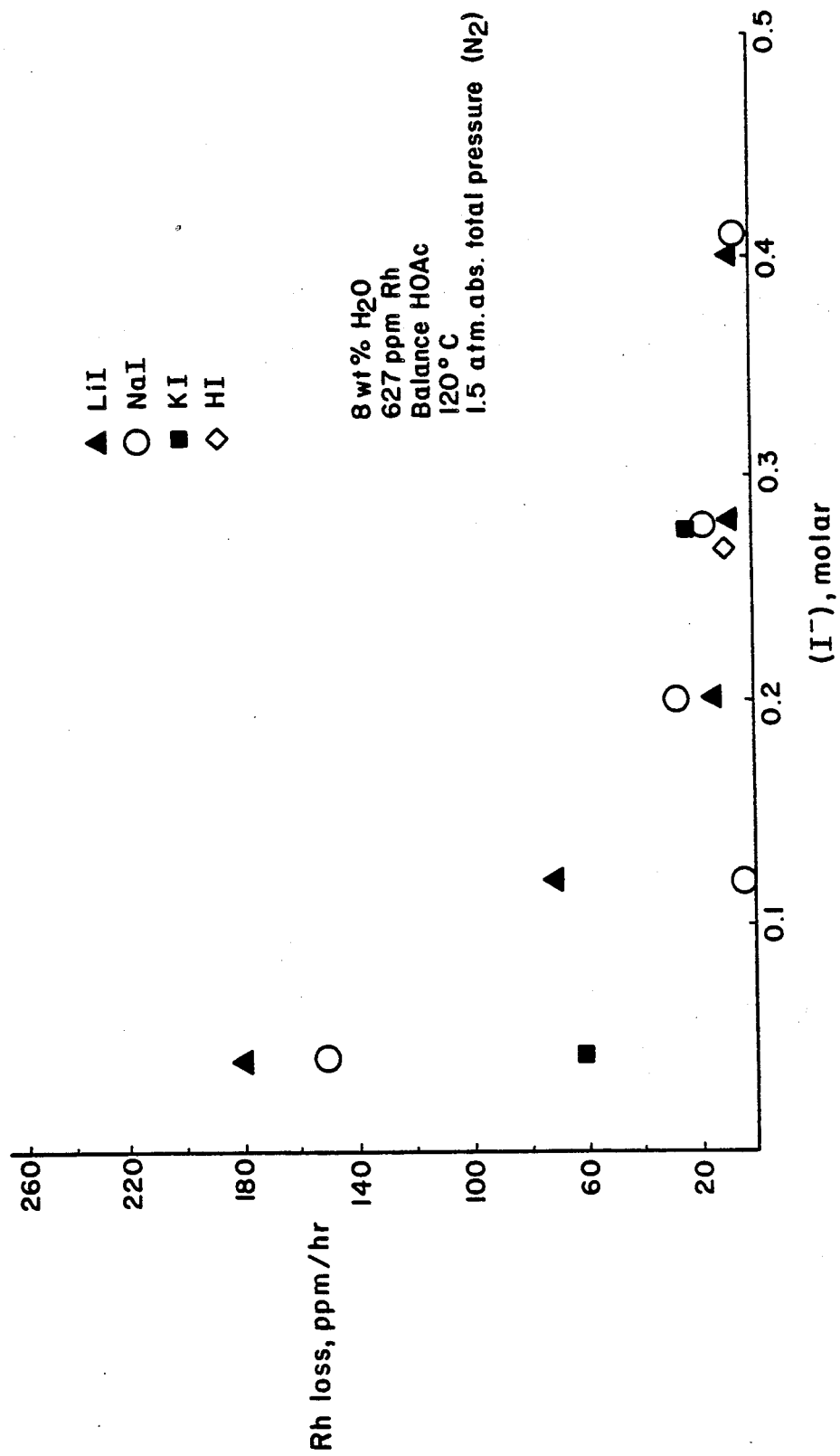

FIG. 11 based on data obtained in the batch autoclave, illustrates that it is the halide (in this case iodide) moiety which is the significant factor in stabilizing the reaction catalyst. Note especially, for example, that at about 0.28 molar concentration of iodide the (low) rhodium loss per hour is essentially the same regardless of the source of the iodide.

Figure 12:
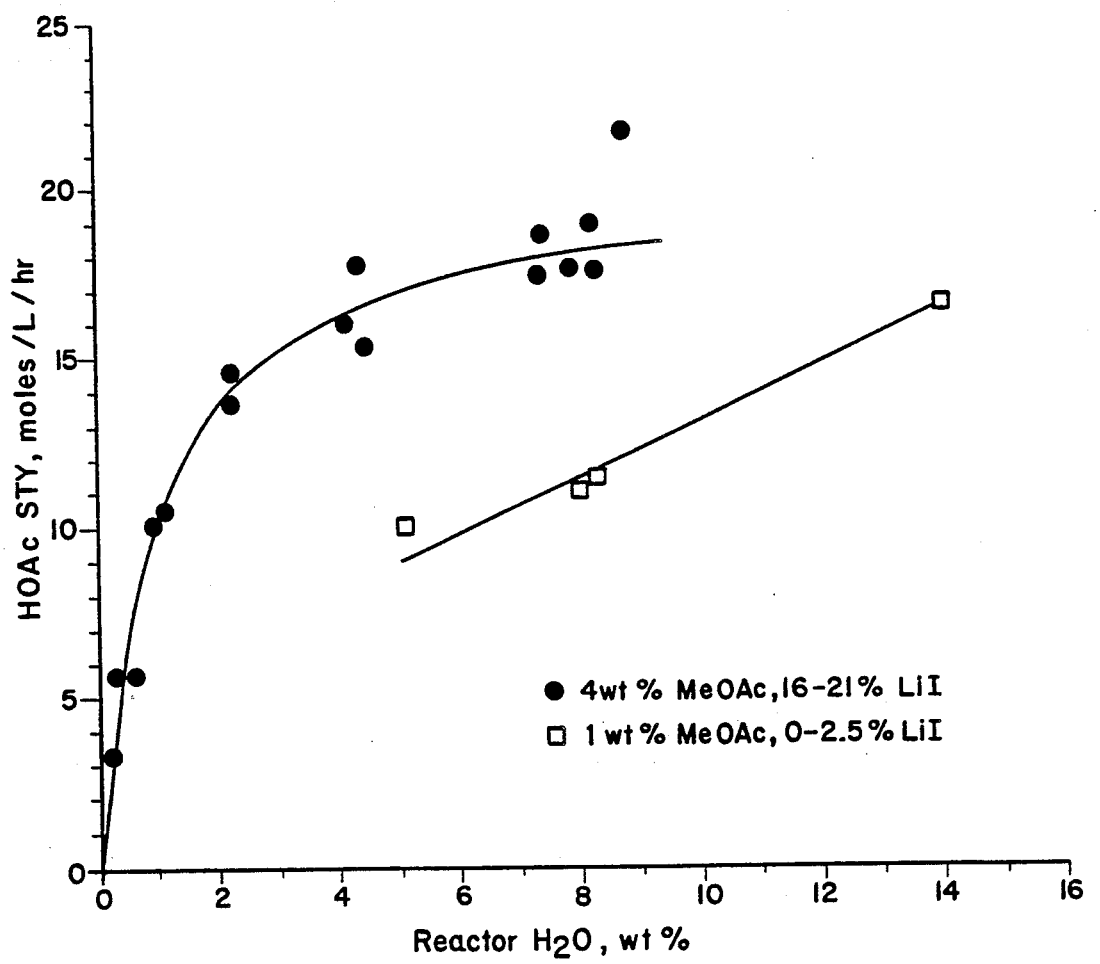

FIG. 12, as well as FIGS. 13–27, presents data taken from the continuous unit the operation of which has been previously described. FIG. 12 itself illustrates that high lithium iodide together with high methyl acetate counteracts the deleterious effects on space-time yield of reducing the water concentration in the reaction medium. It will be seen that with 16 to 21 wt. % lithium iodide and 4 wt. % methyl acetate the space-time yields obtainable at 2 wt. % water in the reaction medium are almost as good as those obtained at higher water concentrations of around, for example 10 wt. % with 1 wt. % methyl acetate and 0–2.5 wt. % lithium iodide. It should be explained, incidentally, that for data points at 4 wt. % methyl acetate conditions set out in FIG. 12 there is a range of lithium iodide concentration. This is due to the fact that the steady state lithium iodide content is determined by an equilibrium between lithium iodide and lithium acetate which is affected by the change in reactor water and methyl acetate content. This will be shown later (FIG. 22). This is also true for similar figures to follow.

Figure 13:
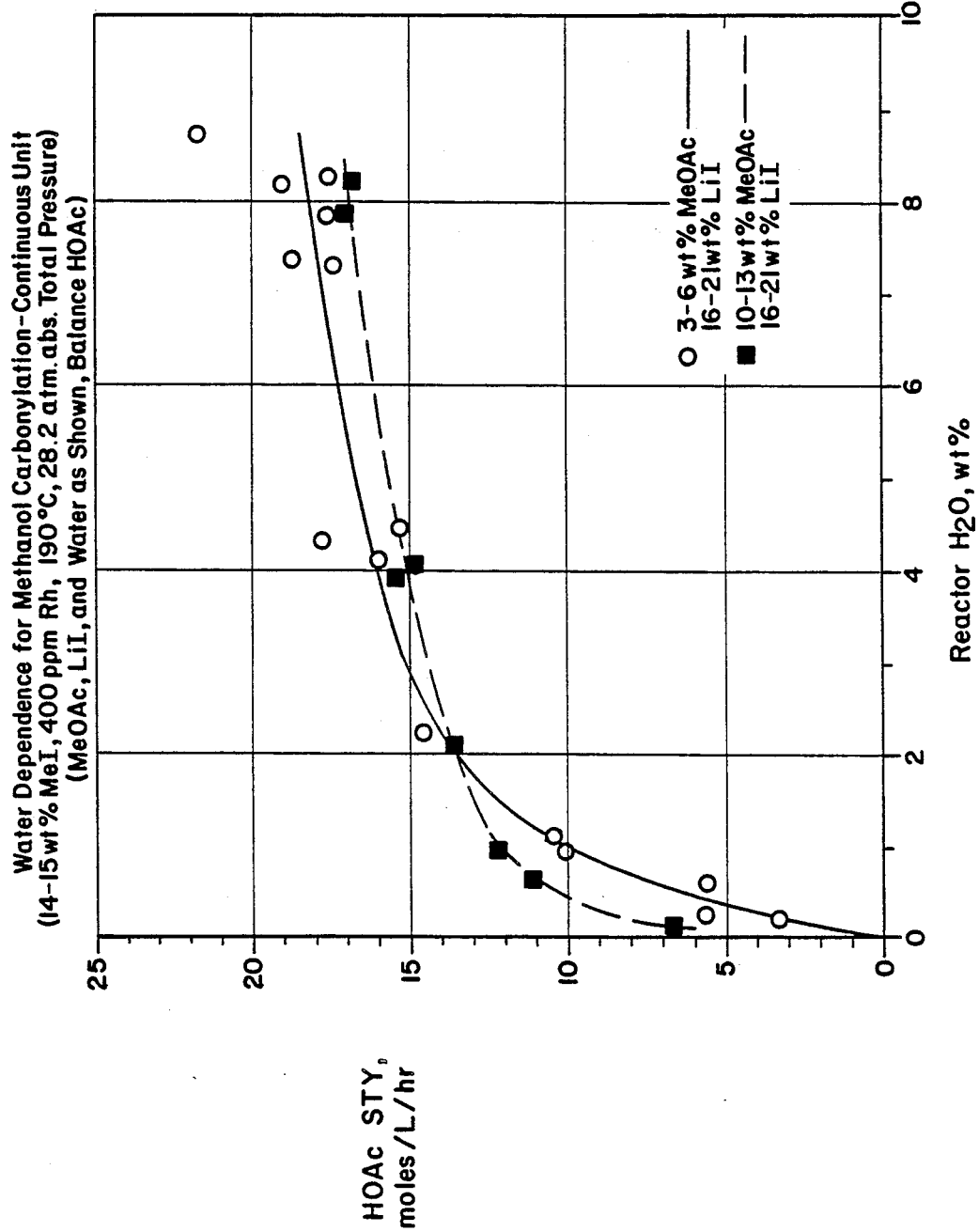

FIG. 13 illustrates that the reaction rate is dependent on water concentration even at high concentrations of lithium iodide, but that at about 1 wt. % water the use of high lithium iodide brings the reaction rate up to about 10 to 12 moles per liter-hour and that above about 2 wt. % water the use of high lithium iodide brings about space-time yields almost as high as those obtained at 8 wt. % water and higher (FIG. 12).

Figure 14:
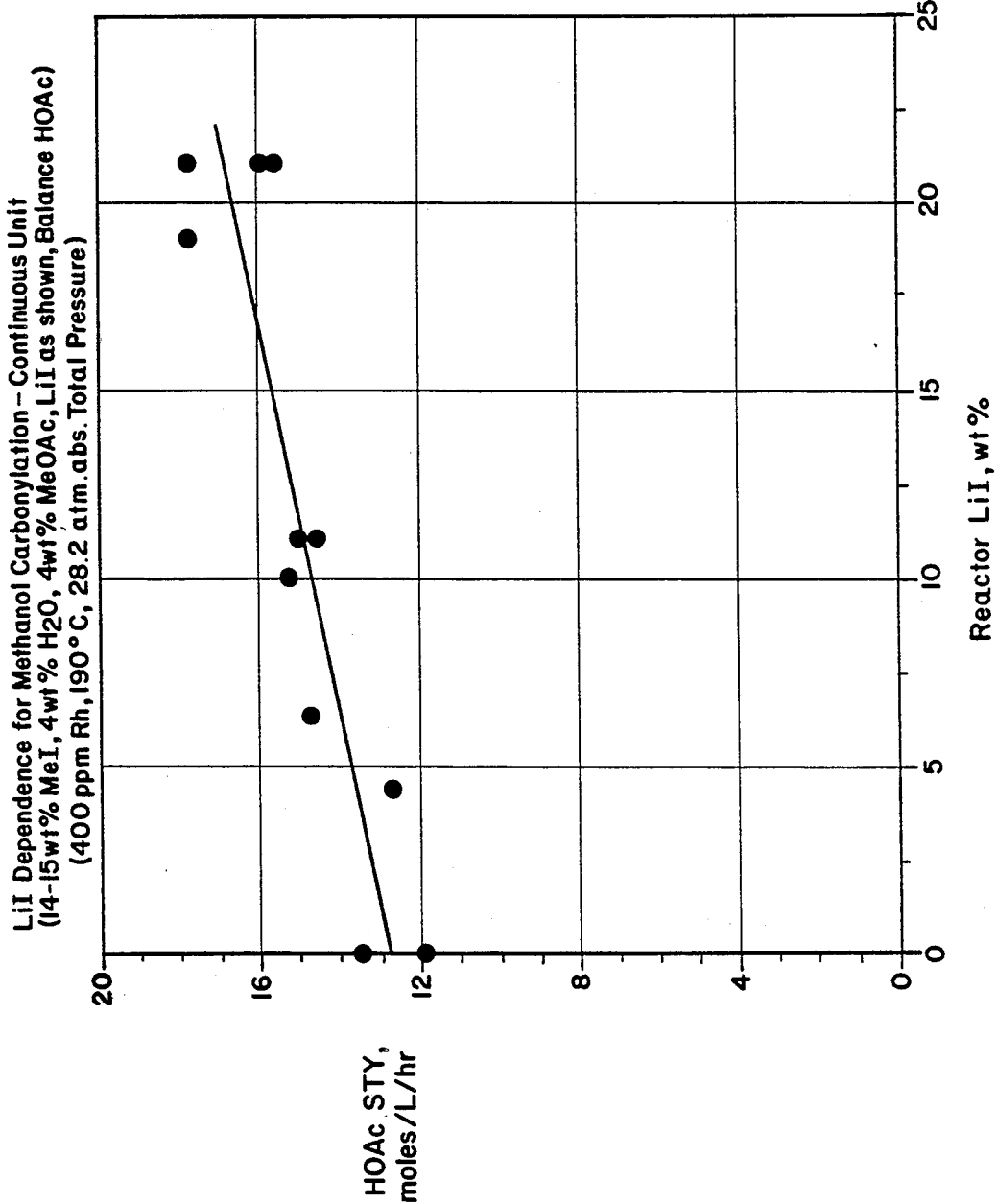
Figure 15:
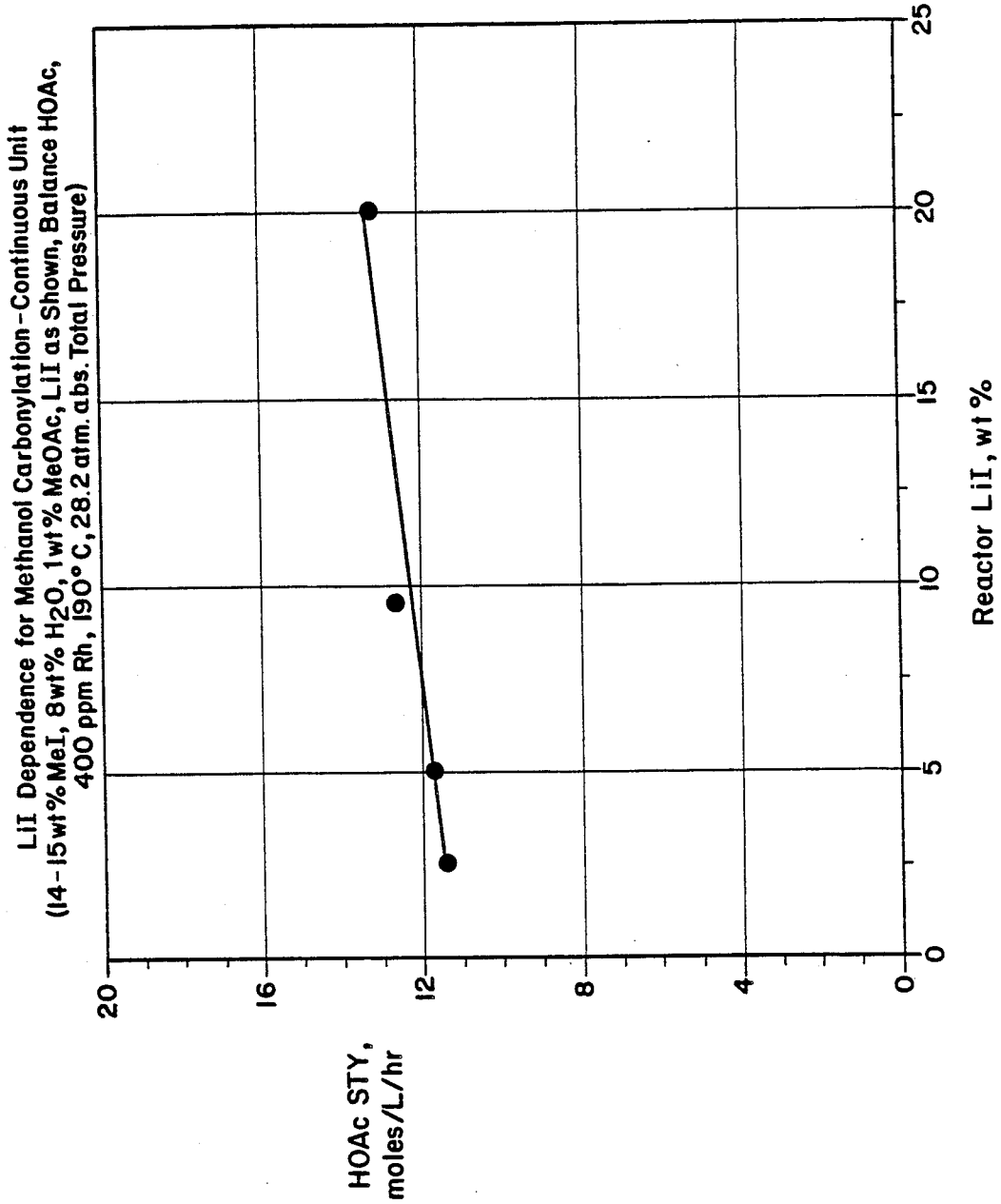

FIGS. 14 and 15 describe the effect of increasing lithium iodide concentration in increasing the space-time yield of acetic acid at two levels of methyl acetate in the reaction medium. These data, which are from the continuous unit, can be read in conjunction with FIG. 4, which presents data from the batch autoclave.

The effect of lithium iodide on the rate of methanol carbonylation under conditions of high water (8 wt. %) and low methyl acetate (1 wt. %) concentration as shown in FIG. 15 would appear to be relatively small in the range of 0–20 wt. % lithium iodide (ca. 18% rate increase) when compared with FIG. 14 and also with FIG. 4 (batch). The differences are mainly due to the different methyl acetate and water concentrations used in the runs in the different figures. The higher the methyl acetate and the lower the water concentration the higher is the effect of lithium iodide on the rate. Because lithium iodide stabilizes the Rh catalyst, it becomes possible to decrease the reactor water concentration in order to increase throughput in the purification train. Also if the water concentration is decreased in conjunction with increasing the methyl acetate concentration, a significant rate enhancement due to lithium iodide is observed as shown in FIG. 14 (4 wt. % water, 4 wt. % methyl acetate, 0–21 wt. % lithium iodide; 23–50% rate increase from 0–21 wt. % lithium iodide) and in FIG. 4 (2–8 wt. % water, 27 wt. % methyl acetate and 2–20% lithium iodide, 200% rate increase from 2–20 wt. % lithium iodide). Therefore, lithium iodide addition makes possible operation in a new concentration range of low water and high methyl acetate (FIG. 12), heretofore impossible because of low rates and severe catalyst instability. Further evidence for rate enhancement due to lithium iodide is given in FIG. 4 which shows that the lower the water concentration and the higher the methyl acetate concentration the greater the rate-enhancing effect of lithium iodide.

Figure 16:
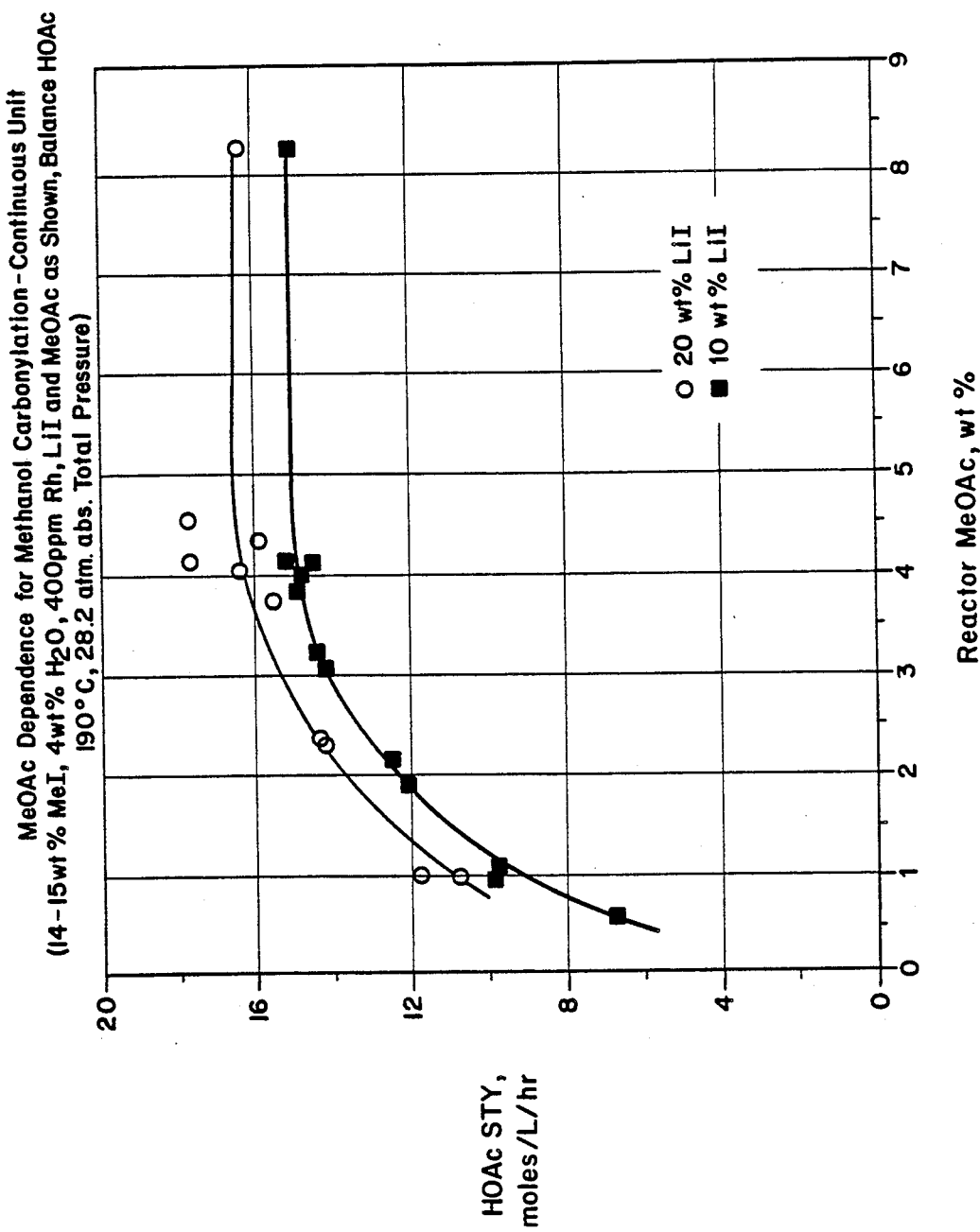
Figure 17:
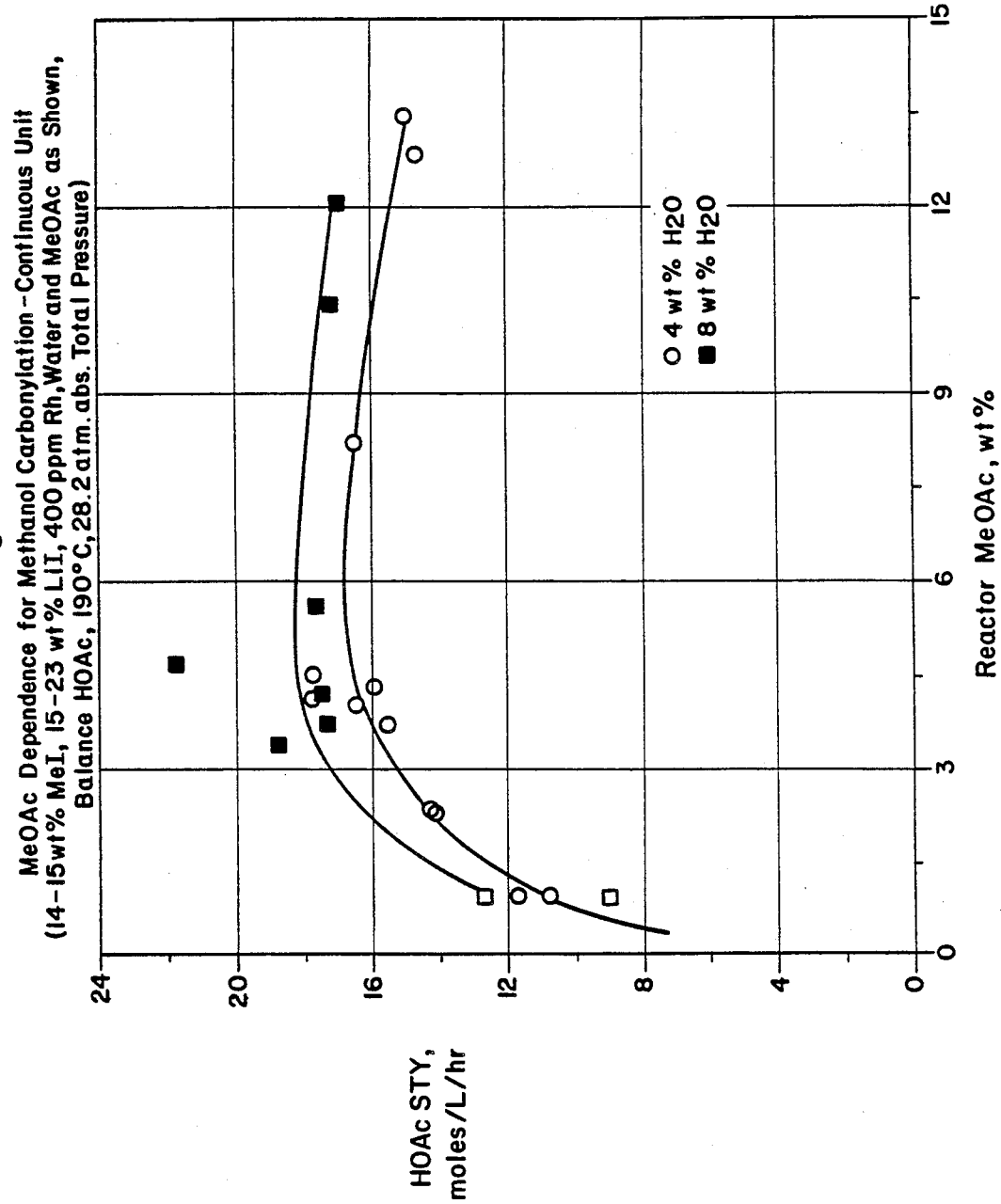

The effect of methyl acetate (in the presence of high lithium iodide concentrations) on the acetic acid space-time yield is shown in FIGS. 16 and 17. In both cases the effect of adding methyl acetate is beneficial up to a level of about 4 to 5 wt. %, after which the effect levels off or (FIG. 17) declines slightly. Between 0 and about 3 wt. %, the beneficial effect of adding methyl acetate is marked. Using 20 wt. % lithium iodide is seen to be more beneficial than using 10 wt. %, and space-time yield is somewhat better with 8 wt. % water as compared with 4 wt. %.

Figure 18:
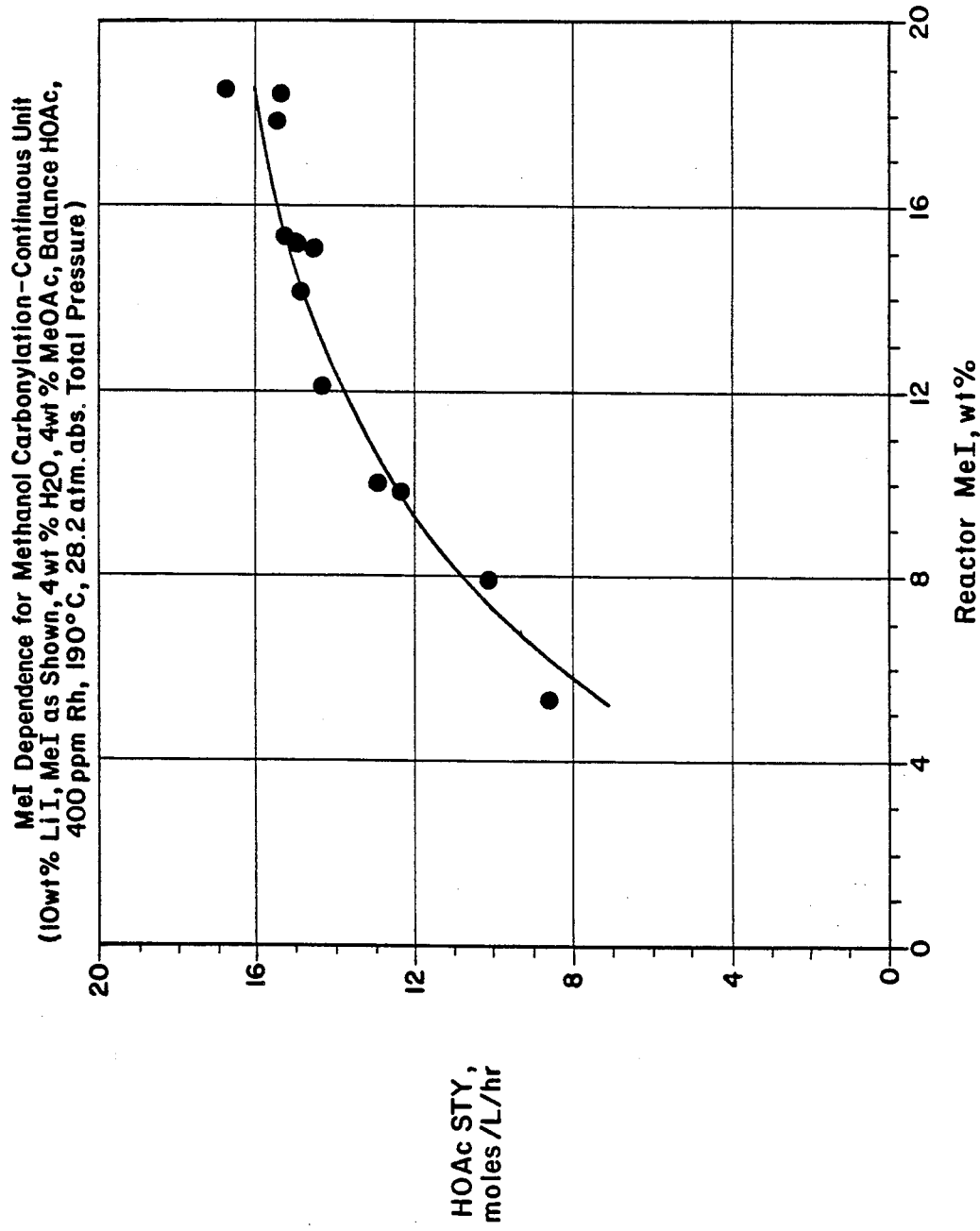

FIGS. 18 and 19 show that the acetic and space-time yield increases when increasing methyl iodide concentration and rhodium concentration respectively, as expected.

FIG. 20 illustrates the effect of lithium iodide, methyl acetate, and water on the (undesired) formation of carbon dioxide as a reaction by-product. When using 16 to 21 wt. % lithium iodide and 4 wt. % methyl acetate the generation of carbon dioxide is much lower than when using 0 to 2.5 wt. % lithium iodide and only 1 wt. % methyl acetate. It is also to be noted that reducing the water content with a given reaction medium has the effect of reducing the rate of formation of carbon dioxide. Reducing carbon dioxide formation in this manner, by using the lithium iodide or equivalent stabilizers of the present invention, is another unexpected result of operating in the low-water reaction medium the use of which is made possible by employing these stabilizers. FIGS. 21, 22, 23, and 24 further show the individual effects of lithium iodide, methyl acetate, and methyl iodide at low water concentration (4 to 8 wt. %) on the formation of carbon dioxide. FIG. 22 also shows the equilibrium concentration of hydrogen iodide at various lithium iodide concentrations.

FIG. 25 deals with the equilibrium existing in the reaction medium between lithium iodide and lithium acetate:

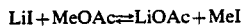

with decreasing water content the lithium acetate content of the reaction medium increases, this effect being greater when 12 wt. % methyl acetate is present as compared with 4 wt. %. This equilibrium between lithium iodide and lithium acetate which is dependent on the water concentration of the reaction medium has been found, incidentally, to have no adverse effect on the behavior of the catalyst system. As a matter of fact this equilibrium will allow the increasing of the lithium iodide concentration of the reaction medium by adding, if desired, lithium acetate or other lithium salts. Because of this equilibrium one cannot distinguish the effect of lithium iodide from that of lithium acetate on the reaction rate and it is possible that both the lithium iodide and lithium acetate increase the reaction rate, especially with catalyst solutions with low water concentration. However, the important fact is that adding either lithium acetate or lithium iodide one obtains eventually the same equilibrium mixture of both salts in solution.

FIGS. 26 and 27 depict the results of studies of rhodium loss from the reaction medium in the continuous unit, FIG. 26 demonstrating that increasing the lithium iodide concentration greatly reduces rhodium loss at varying water concentrations and at two different methyl acetate concentrations while FIG. 27 demonstrates that at higher water concentrations there is less rhodium loss and also that going to the relatively high methyl acetate concentration of 12 wt. % increases rhodium loss as compared with using 4 wt. % methyl acetate.

EXAMPLE 27

The following run was carried out in continuously-operating apparatus comprising a stirred reactor from which the product was drawn off continuously for workup in the manner previously described hereinabove. The carbonylation reactor contained approximately 1800 ml of liquid reaction medium, measured at ambient temperature in the bubble-free state. Its contents were analyzed periodically throughout the run, and these analyses were employed to control the flows of the several streams entering the reactor in such a manner as to maintain in the liquid reaction medium about 13 to 16 wt. % methyl iodide, 4 to 5 wt. % methyl acetate, 19 to 19.5 wt. % lithium iodide, 4 to 5 wt. % water, and 310 to 335 ppm of rhodium. The balance of the reaction medium was acetic acid. Before starting the run, the carbonylation reactor had been initially charged with a mixture of about 16 wt. % water, 12 wt. % methyl iodide, 0.7 wt. % methyl acetate, and the balance acetic acid, the total mixture containing about 400 ppm of rhodium in the form of a rhodium carbonyl iodide compound. The rhodium compound can be prepared by dissolving rhodium triiodide in acetic acid containing 15–20 wt. % water at about 110° C. while sparging carbon monoxide through the mixture at a pressure of about one atmosphere or higher.

During operation the reactor temperature was maintained between about 189° C. and 191° C. The pressure was maintained at about 28 atmospheres. Carbon monoxide was continuously introduced through a sparger situation below the agitator blades, and a continuous vent of gas was drawn off from the top of the vapor space contained in the upper part of the reactor at about 15 liters per hour (ambient temperature and pressure). The carbon monoxide partial pressure in the reactor head space was maintained at about 13 atmospheres.

By means of a level control sensing the liquid level within the reactor, liquid reaction product was continuously drawn off and fed onto the tray of a single-tray flasher operating at a head pressure of about 2.4 atmospheres. Of the liquid fed into the flasher, approximately 35% was distilled overhead for further redistillation in the methyl iodide-acetic acid splitter column while the remainder was drawn from the base of the column and returned to the carbonylation reactor. This stream comprised predominantly acetic acid and contained the catalyst.

The methyl iodide-acetic acid splitter column contained 20 trays, with the overhead from the flasher just described being introduced onto the 15th tray from the bottom. This splitter column was operated at a head pressure of 1 atmosphere and with a reflux ratio of 1:1. Of the feed initially introduced into this column, approximately 60% was taken overhead and was recycled to the carbonylation reactor. This stream contained predominantly methyl iodide and lesser quantities of methyl acetate. Such methyl iodide makeup as was necessary to maintain the desired methyl iodide content in the carbonylation reactor was introduced into this recycling stream before it was returned to the carbonylation reactor. The rate of methyl iodide introduction was set by periodic analyses of the vent streams leaving the reactor and the flasher, enough methyl iodide being introduced to make up for these process losses. Also introduced into this stream just before entering the carbonylation reactor was sufficient methanol to maintain the desired methyl acetate content in the reactor liquid medium. (Methanol is converted almost immediately to methyl acetate upon entering the reactor). Such water as was needed to maintain the desired water content in the reactor was also introduced with this methyl iodide recycle stream.

Preferably, water recovered in any of the distillate streams is recycled to the reactor. There is very little consumption of water in the reaction. If a water phase forms at any point in the product-recovery system, it will probably contain methyl iodide, which should be returned to the reactor.

The residue stream from the methyl iodide-acetate acid splitter column was drawn off as the crude acetic acid product, to be purified further as desired by conventional methods outside the scope of the present invention. As previously explained, a primary object of the operation was to produce a crude acetic acid at this point containing only a small amount of water.

With the system operating as just described, the STY of acetic acid in the crude acetic acid product drawn from the base of the methyl iodide-acetic acid splitter was approximately 14 gram-moles of acetic acid (calculated as pure acetic acid) per hour per liter of liquid reaction medium contained in the carbonylation reactor, the volume of said liquid reaction medium being measured at ambient temperature. The water content of the crude acetic acid was approximately 4 to 7 wt. %. This is to be compared with a water content of 20 to 25 wt. % and an STY of 13 with the same rhodium concentration where, in accordance with the usual practice of the prior art, the carbonylation reactor was operated with a water content of approximately 15 wt. % in the reaction medium.

As indicated by periodic analyses of the contents of the carbonylation reactor, there was very little precipitation of catalyst from the reaction medium in the flasher column and in the transfer lines recycling the catalyst solution from this column back to the carbonylation reactor, although our experience with solutions without iodide salts as in the prior art would have led one to predict a serious catalyst-loss problem.

When using other iodide salts, the controlling factor is the concentration of iodide moiety supplied by whatever salt is employed. That is, the beneficial results obtained with a given concentration of lithium iodide will also be obtained with other iodide salts when they are used in a concentration such that the molar equivalent iodide concentration is the same as that obtaining with a given lithium iodide concentration known to be effective.

An unexpected effect of operating the reaction system by the low-water method just described is also that there is a great reduction (by an order of magnitude) in the rate of formation of by-product propionic acid, the presence of which in the product acetic acid is objectionable for several reasons. Again as compared with the relatively high-water operating conditions of the prior art, there is a substantial reduction in the rate of formation of hydrogen and carbon dioxide, which, are undesirable reaction products. These are formed by the water-gas shift reaction from carbon monoxide and water. The following tabulation (Table III) compares yields of propionic acid (HOPr), carbon dioxide, and hydrogen obtained at the above conditions of 4 to 5 wt. % water with those obtained using 14 to 15 wt. % water in the reaction system characteristic of the prior art (no iodide salt). Methyl acetate content of the reaction medium was about 1 wt. % in the high water medium and about 4 wt. % in the low water system.

TABLE III

| Reactor H$_2$O | CO$_2$ Make (Moles CO$_2$/ 100 moles HOAc) | H$_2$ Make (Moles H$_2$/ 100 moles HOAc) | HOPr (ppm) | Acetic Acid % Yield Based on MeOH |
|---|---|---|---|---|
| 14–15% (No iodide salt) | 2.3 | 1.9 | 1435(1) | 99(2) |
| 4–5% (Iodide salt as described above) | 0.2 | 0.1 | 91(1) | 99(2) |

(1) In acid product from base of MeI—HOAc splitter.
(2) Approximate, within experimental margin of error. As calculated, yield was slightly higher in the "low water" case.

EXAMPLE 28

Other iodide salts are as efficacious as lithium iodide. at the same iodide moiety concentration in the reaction medium For example, in the continuous reaction system described in Example 27 a run was made in which the iodide salt was sodium iodide. Operating in the same manner as described with lithium iodide in Example 27, but with the iodide concentration being reduced because of the limited solubility of sodium iodide as compared with lithium iodide, the run was made under conditions as set forth in Table IV below. The reaction-medium was as tabulated below, with acetic acid making up the balance in each tabulated case.

The results as tabulated show that, at the same concentration of iodide moiety, sodium iodide gave results as good as those obtained with lithium iodide, specifically, within the indicated limits of accuracy, results were identical. When using the higher water concentration characteristic of the prior art but with no iodide salt, the acetic acid space-time yield was slightly higher, but it is to be kept in mind that this was at the expense of having to work in the recovery system with a crude reaction medium containing 14 wt. % water instead of 4 wt. %. It is also to be kept in mind that in actual application of the present invention the iodide concentration would have preferably been higher than the indicated 9.4 wt. %, which was the maximum concentration which could be used in the present Example in order to maintain comparability with sodium iodide, the solubility characteristics of which precluded using the higher concentrations which would actually be preferred.

TABLE IV

| Promoter/Stabilizer Iodide Salt | NaI | LiI |
|---|---|---|
| Inorganic Iodide (wt. %) | 9.5 | 9.4 |
| Temperature (°C.) | 190 | 190 |
| Pressure (atm) | 28 | 28 |
| Water, (wt. %) | 4.0 | 4.0 |
| Methyl Iodide (wt. %) | 12.2 | 12.1 |
| Methyl Acetate (wt. %) | 3.1 | 3.1 |
| Rhodium (ppm) | 400 | 400 |
| Acetic Acid STY (mol/l · hr) | 14.3 | 12.7 |
| Carbon Dioxide STY (mol/l · hr) | 0.39 | 0.35 |
| Propionic Make Rate (lbs/MM lbs acetic acid) | 150 | 109 |
| Rhodium Loss, (ppm/hr) | 0.75 | 0.73 |

The effect of using a variety of iodide salts is set forth in Table V below. These data are all from runs which were carried out in the batch autoclave operated in the manner previously described. These data indicate that other iodide salts have a rate acceleration (promoting) action as well as does lithium iodide. FIG. 11 shows stabilizing action of several specific iodides. However, many of these do not have a very high solubility when the reaction medium is cooled much below normal operating temperature. Lithium iodide continues to be preferred because of its superior solubility characteristics.

TABLE V

Rate of Methanol Carbonylation With Various Iodide Sources
Batch Autoclave
Charge: 19 wt. % MeI, 472 ppm Rh, 27 wt. % MeOAC, 0.75 M I$^-$ (equiv. to 10 wt. % LiI)
28.2 atm. abs., 190° C.

| Salt | 2 wt. % H$_2$O STY | 4–5 wt. % H$_2$O STY | Comments |
|---|---|---|---|
| no salt | 3.0 | 10.9 | |
| LiI | 12.2 | 14.8 | soluble |
| NaI | 8.8 | — | soluble |
| KI | 11.2 | 13.2 | partially soluble |

TABLE V-continued

Rate of Methanol Carbonylation With Various Iodide Sources
Batch Autoclave
Charge: 19 wt. % MeI, 472 ppm Rh, 27 wt. % MeOAC, 0.75 M I⁻
(equiv. to 10 wt. % LiI)
28.2 atm. abs., 190° C.

| Salt | 2 wt. % $H_2O$ STY | 4-5 wt. % $H_2O$ STY | Comments |
|---|---|---|---|
| RbI | — | 4.3 | poor solubility |
| CsI | — | — | insoluble |
| $MgI_2$ | 10.7 | 12.7 | partially soluble |
| $CaI_2$ | 17.2 | — | soluble |
| $SrI_2$ | 7.0 | — | soluble |
| $BaI_2$ | 11.2 | 15.9 | soluble |
| $CoI_2$ | 12.6 | — | soluble |
| $SbI_3$ | — | — | insoluble |
| $ZnI_2$ | 5.1 | 11.5 | soluble |
| $SnI_2$ | 1.3 | — | soluble |
| $FeI_2$ | 3.8 | 13.5 | partially soluble |
| $LaI_3$ | — | 16.7 | partially soluble |
| $NiI_3$ | — | 3.5 | insoluble |
| $MnI_2$ | 8.9 | — | soluble |
| NMPI | 10.1 | — | soluble |
| $(Ph)(CH_3)_3N^+I^-$ | 6.1 | — | partially soluble |
| $Bu_4N^+I^-$ | 7.1 | — | soluble |
| $(Et)(Ph)_3P^+I^-$ | 8.9 | — | soluble |
| $NH_4{}^+I^-$ | 4.67 | — | insoluble |

What is claimed is:

1. In a process for producing acetic acid by reacting a feed consisting essentially of methanol with carbon monoxide in a carbonylation reactor holding a liquid reaction medium containing a rhodium catalyst, the improvement which comprises:

maintaining catalyst stability and system productivity by maintaining in said reaction medium during the course of said reaction at least a finite concentration up to less than 14 wt. of water together with (a) from about 2 to 20 wt. % of lithium iodide as a catalyst stabilizer, (b) from about 5 to 20 wt. % methyl iodide, and (c) from about 0.5 to 30 wt. % methyl acetate, and (d) a partial pressure of hydrogen of at least about 4 up to about 150 psi at reaction conditions comprising 15 to 40 atmospheres total reaction pressure.

2. The improvement of claim 1 wherein said hydrogen is maintained at a partial pressure of at least about 4 to about 40 psi.

3. The improvement of claim 1 wherein said hydrogen is maintained at a partial pressure of at least about 20 to about 40 psi.

4. The improvement of claim 1 wherein said hydrogen is maintained at a partial pressure of at least about 10 psi.

5. The improvement of claim 1 wherein said hydrogen is maintained at a partial pressure of at least about 20 psi.

6. The improvement of claim 1 wherein said hydrogen is maintained at a partial pressure of at least about 40 psi.

7. The improvement of claim 1 wherein hydrogen is co-fed with said carbon monoxide in an amount of at least about 0.3 mol % based on the carbon monoxide and hydrogen feed mixture to maintain said hydrogen partial pressure.

8. The improvement of claim 1 wherein hydrogen is co-fed with said carbon monoxide in amounts of from about 0.3 mol % to about 10 mol % based on the carbon monoxide and hydrogen feed mixture to maintain said hydrogen partial pressure.

9. The improvement of claim 1 wherein the balance of said reaction medium consists essentially of acetic acid, and wherein the rhodium catalyst is maintained in said reaction in a concentration of about 200 ppm to about 1000 ppm calculated as rhodium.

10. The improvement of claim 9 wherein hydrogen is co-fed with said carbon monoxide in amounts of from about 1 mol % to about 5 mol % based on the carbon monoxide and hydrogen feed mixture to maintain said hydrogen partial pressure.

11. The improvement of claim 9 wherein, in weight percent, there is maintained in the reaction medium about 1 to 4 wt. % water, 10 to 20 wt. % lithium iodide, 12 to 16 wt. % methyl iodide, and 0.5 to 5 wt. % methyl acetate when optimal catalyst stabilization is desired or 2 to 5 wt. % methyl acetate when maximal reactor productivity is desired, with the balance consisting essentially of acetic acid.

12. The improvement of claim 11 wherein said hydrogen is maintained at a partial pressure of at least about 10 psi.

13. The improvement of claim 11 wherein said hydrogen is maintained at a partial pressure of at least about 20 psi.

14. The improvement of claim 11 wherein said hydrogen is maintained at a partial pressure of at least about 40 psi.

15. The improvement of claim 11 wherein hydrogen is co-fed with said carbon monoxide in an amount of at least about 0.3 mol % based on the carbon monoxide and hydrogen feed mixture to maintain said hydrogen partial pressure.

16. The improvement of claim 11 wherein hydrogen is co-fed with said carbon monoxide in amounts of from about 0.3 mol % to about 10 mol % based on the carbon monoxide and hydrogen feed, mixture to maintain said hydrogen partial pressure.

17. The improvement of claim 11 wherein hydrogen is co-fed with said carbon monoxide in amounts of from about 1 mol % to about 5 mol % based on the carbon monoxide and hydrogen feed mixture to maintain said hydrogen partial pressure.

* * * * *